(12) United States Patent
Shen

(10) Patent No.: US 10,336,766 B2
(45) Date of Patent: Jul. 2, 2019

(54) ANTICANCER DRUG CANDIDATES

(71) Applicant: THE SCRIPPS RESEARCH INSTITUTE, La Jolla, CA (US)

(72) Inventor: Ben Shen, Jupiter, FL (US)

(73) Assignee: The Scripps Research Institute, La Jolla, CA (US)

(*) Notice: Subject to any disclaimer, the term of this patent is extended or adjusted under 35 U.S.C. 154(b) by 0 days.

(21) Appl. No.: 15/541,904

(22) PCT Filed: Jan. 8, 2016

(86) PCT No.: PCT/US2016/012634
§ 371 (c)(1),
(2) Date: Jul. 6, 2017

(87) PCT Pub. No.: WO2016/112282
PCT Pub. Date: Jul. 14, 2016

(65) Prior Publication Data
US 2018/0009823 A1    Jan. 11, 2018

Related U.S. Application Data

(60) Provisional application No. 62/100,932, filed on Jan. 8, 2015.

(51) Int. Cl.
  *C07D 491/08* (2006.01)
  *A61K 47/68* (2017.01)
  *A61K 31/122* (2006.01)

(52) U.S. Cl.
  CPC .......... *C07D 491/08* (2013.01); *A61K 31/122* (2013.01); *A61K 47/6803* (2017.08); *A61K 47/6851* (2017.08)

(58) Field of Classification Search
  CPC .............. C07D 491/08; A61K 47/6803; A61K 47/6851
  See application file for complete search history.

(56) References Cited

U.S. PATENT DOCUMENTS

2013/0209494 A1* 8/2013 Chowdari ........ A61K 47/48384
                                              424/178.1

OTHER PUBLICATIONS

Davies et al. Organic Letters, vol. 7, No. 23, 2005, pp. 5233-5236.*

* cited by examiner

*Primary Examiner* — Samira J Jean-Louis
(74) *Attorney, Agent, or Firm* — Geoffrey K. Cooper; Thomas Fitting

(57) ABSTRACT

Enediyne compounds having a structure according to formula (I), where $R_1$, $R_2$, $R_3$, $R_4$, $R_5$, $R_6$, $R_7$ and X are defined herein.

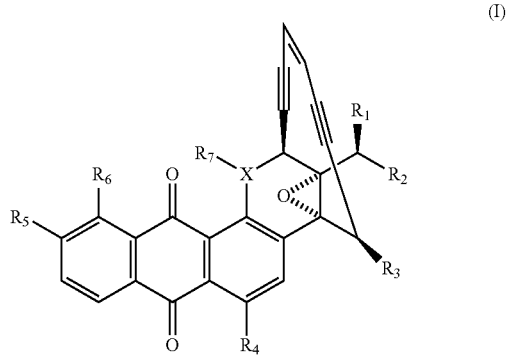

(I)

5 Claims, 6 Drawing Sheets

C

Tiancimycin A    Tiancimycin B    Tiancimycin C

D

ANTICANCER DRUG CANDIDATES

This is a United States national stage entry of international PCT Application PCT/US2016/012634, filed Jan. 8, 2016, which claims the benefit of priority from U.S. Provisional Patent Application No. 62/100,932, filed Jan. 8, 2015, entitled, "Anticancer Drug Candidates," both of which are incorporated herein by reference in their entireties.

FIELD OF THE INVENTION

Embodiments of the invention are directed to compounds for the treatment of cancer. In particular embodiments, the compounds are derived from enediynes.

BACKGROUND

The enediyne natural products are the most cytotoxic molecules in existence today, and their use as anticancer drugs has been demonstrated clinically. The natural enediynes have seen limited use as clinical drugs mainly because of substantial toxicity, however, various polymer-based delivery systems or antibody-drug conjugates (ADCs) have shown great clinical success or promise in anticancer therapy. Indeed, the poly(styrene-co-maleic acid)-conjugated neocarzinostatin (SMANCS®) has been marketed since 1994 for use against hepatoma. Various ADCs have been developed or are in varying stages of development, including a CD33 mAB-calicheamicin (CAL) conjugate (i.e., MYLOTARG®) for acute myeloid leukemia (AML), a CD22 mAB-CAL conjugate (inotuzumab ozogamicin) for non-Hodgkin lymphoma, as well as, several mAB-C-1027 conjugates for hepatoma and mAB-uncialamycin (UCM) conjugates for selected tumors. These examples clearly demonstrate that the enediynes can be developed into powerful drugs when their extremely potent cytotoxicity is harnessed and delivered to tumor cells.

SUMMARY

Embodiments of the invention are directed to anticancer drugs and to drug discovery. In particular embodiments, the drugs are enediynes or derived from enediynes. Methods of treatment comprise administering the drugs directly to the patient or as a conjugate, such as, for example, antibody-drug conjugates.

Other aspects are described infra.

BRIEF DESCRIPTION OF THE DRAWINGS

(FIG. 1A) Design of PCR primers for enediyne PKS gene cassette targeting E5/E or E/E10, respectively, as well as the primers for the 1-kb internal fragment of E. (FIG. 1B) Representative melting curve analysis in real-time PCR in a 384-well plate format, as exemplified by using the E/E5 primers, with each of the peaks indicating a specific PCR product. (FIG. 1C) Confirmation of PCR products by gel electrophoresis and DNA sequencing. (FIG. 1D) Phylogenetic analysis of the 94 new enediyne producers in comparison with the 11 known ones, affording 31 distinct clades. The phylogenetic tree was based on the amino acid sequences of the 1-kb internal fragment of E and collapsed into 31 distinct clades upon using a 95% sequence identity cutoff. Numbers in parentheses are hits identified from each of the clades. The 11 known enediynes whose gene clusters have been cloned are neocarzinostain (NCS), C-1027, kedarcidin (KED), maduropeptin (MDP), the sporolides (SPO), the cyanosporasides (CYA and CYN), calicheamicins (CAL), the esperamicins (ESP), dynemicin (DYN), and uncialamycin (UCM) (FIG. 1D). *Streptomyces* sp. CB03234, from which the new enediyne tiancimycins were isolated, is highlighted with a * within the box.

(FIG. 3A) The determined structure of tiancimycin A, B, and C. (FIG. 3B) The known enediyne natural product uncialamycin whose structure, including absolute stereochemistry, has been confirmed by total synthesis. (FIG. 3C) Key $^1$H-$^1$H COSY, HMBC, and NOESY correlations supporting the deduced structure of tiancimycin A, B, and C. (FIG. 3D) The CD spectra of tiancimycin A, B, and C in comparison with uncialamycin supporting their assigned absolute stereochemistry.

(FIG. 4A) Isolation of S. sp. CB03234-D15 and CB03234-D25 by DES-mutagenesis of S. sp. CB03234 wild-type and (FIG. 4B) confirmation of tiancimycin A (♦) production of S. sp. CB03234-D15 and CB03234-D25 by submerged fermentation and HPLC and LC-MS analysis with estimated titer of tiancimycin A approximately 10-fold higher in the CB03234-D25 strain than the CB03234 wild-type strain.

DETAILED DESCRIPTION

Figures 1A, 1B, 1C:
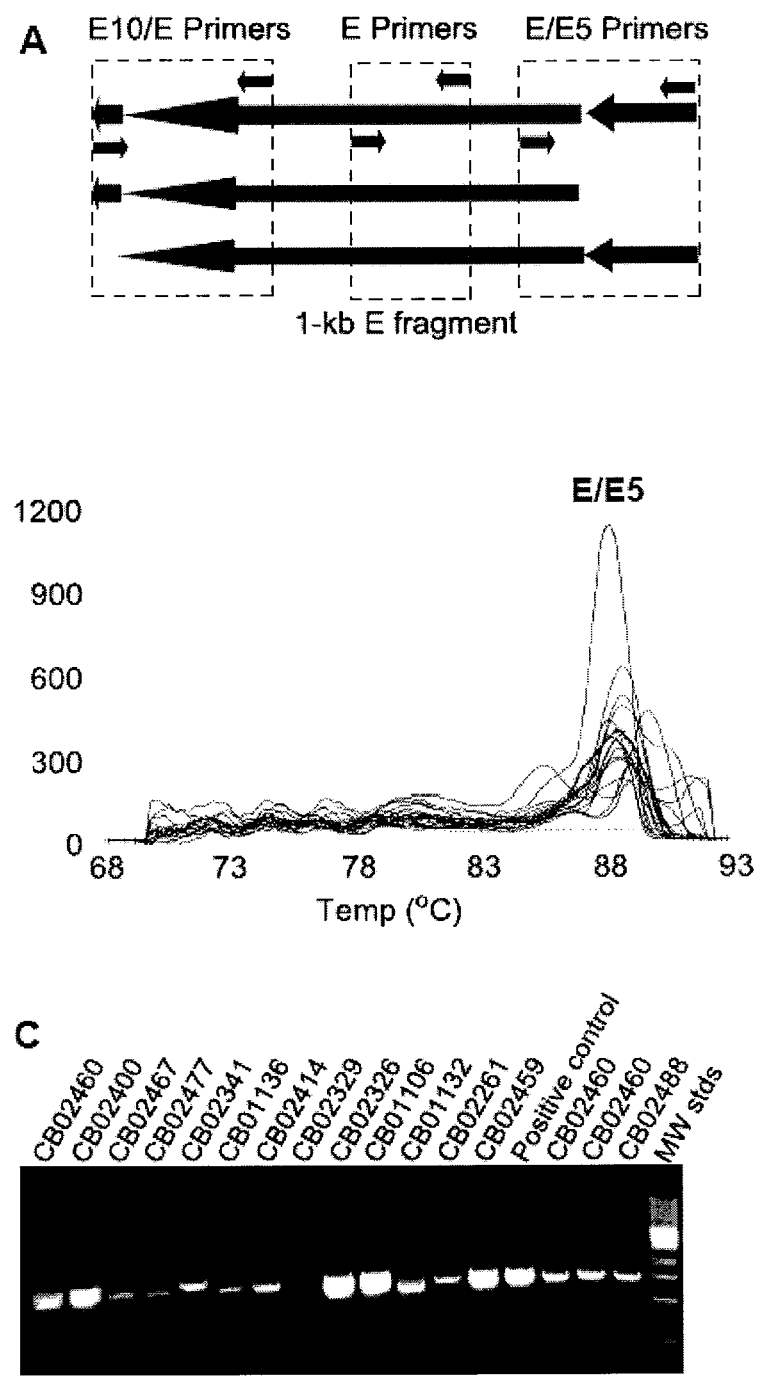
FIGS. 1A-1D show a genome survey of 3,500 strains in the TSRI *Actinomycetale* collection, identifying 94 novel enediyne producers.
Figure 1D:
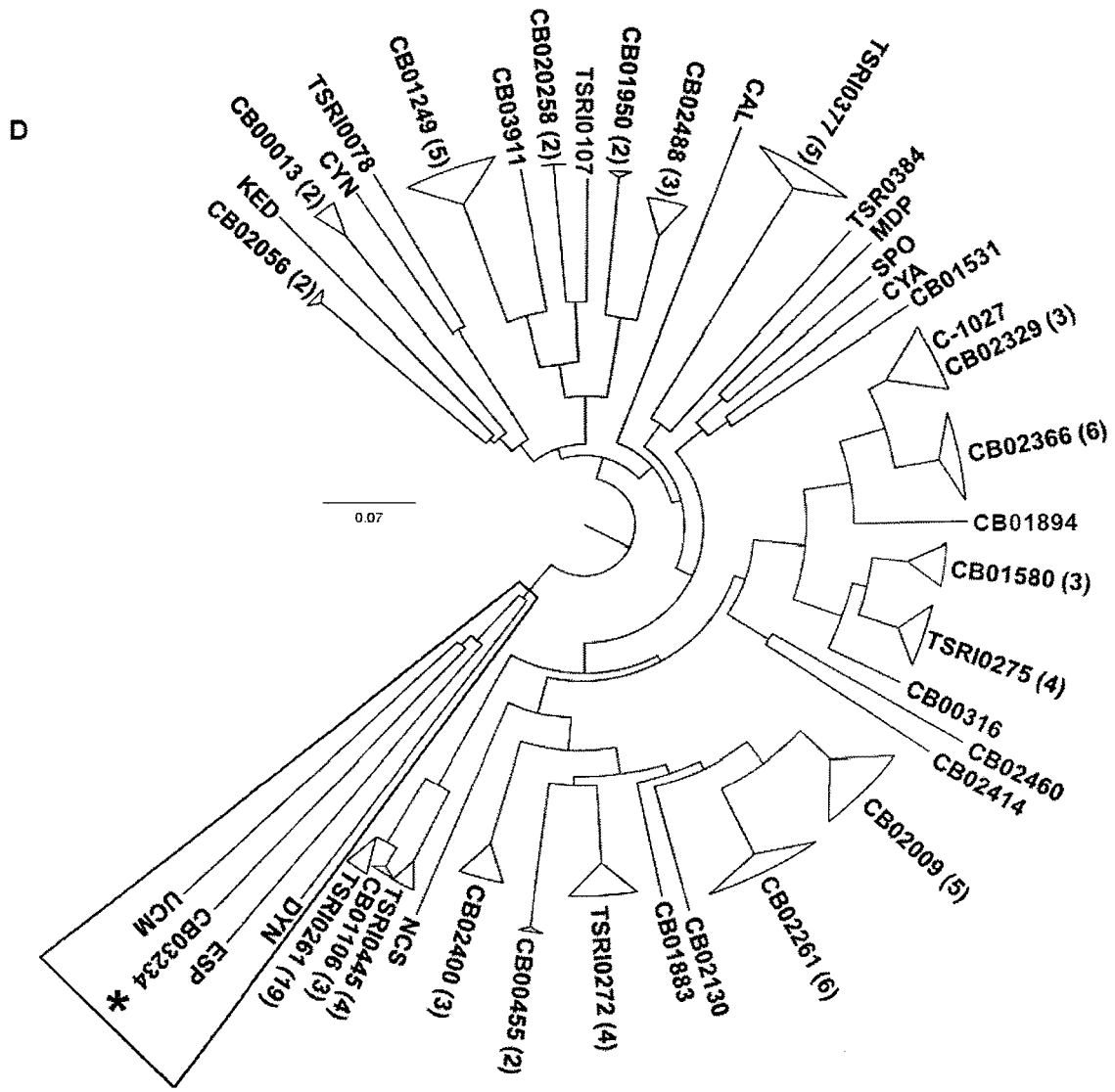

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Embodiments of the invention may be practiced without the theoretical aspects presented. Moreover, the theoretical aspects are presented with the understanding that applicants do not seek to be bound by the theory presented.

All genes, gene names, and gene products disclosed herein are intended to correspond to homologs from any species for which the compositions and methods disclosed herein are applicable. It is understood that when a gene or gene product from a particular species is disclosed, this disclosure is intended to be exemplary only, and is not to be interpreted as a limitation unless the context in which it appears clearly indicates. Thus, for example, for the genes disclosed herein, are intended to encompass homologous and/or orthologous genes and gene products from other organisms.

General Techniques

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, phage display, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, New York, Gait, "Oligonucleotide Synthesis: A Practical Approach" 1984, IRL Press, London, Nelson and Cox (2000), Lehninger, Principles of Biochemistry $3^{rd}$ Ed., W. H. Freeman Pub., New York, N.Y. and Berg et al. (2006) Biochemistry, $6^{th}$ Ed., W. H. Freeman Pub., New York, N.Y., all of which are herein incorporated in their entirety by reference for all purposes.

General methods in molecular and cellular biochemistry can be found in such standard textbooks as Molecular Cloning: A Laboratory Manual, 4th Ed. (Sambrook et al., Cold Spring Harbor Laboratory Press 2012); Short Protocols in Molecular Biology, 5th Ed. (Ausubel et al. eds., John Wiley & Sons 2002); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

As used in this specification and the appended claims, the term "or" is generally employed in its sense including "and/or" unless the content clearly dictates otherwise.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, e.g. within 5-fold, within 2-fold etc., of a value. Where particular values are described in the application and claims, unless otherwise stated the term "about" meaning within an acceptable error range for the particular value should be assumed. All numeric values are herein assumed to be modified by the term "about", whether or not explicitly indicated.

The recitation of numerical ranges by endpoints includes all numbers within that range (e.g., 1 to 5 includes 1, 1.5, 2, 2.75, 3, 3.80, 4, and 5). Although some suitable dimensions ranges and/or values pertaining to various components, features and/or specifications are disclosed, one of skill in the art, incited by the present disclosure, would understand desired dimensions, ranges and/or values may deviate from those expressly disclosed.

By "encoding" or "encoded", "encodes", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code.

"Target molecule" includes any macromolecule, including protein, peptide, polypeptide, gene, polynucleotide, oligonucleotide, carbohydrate, enzyme, polysaccharide, glycoprotein, receptor, antigen, tumor antigen, markers, molecules associated with a disease, an antibody, growth factor; or it may be any small organic molecule including a hormone, substrate, metabolite, cofactor, inhibitor, drug, dye, nutrient, pesticide, peptide; or it may be an inorganic molecule including a metal, metal ion, metal oxide, and metal complex; it may also be an entire organism including a bacterium, virus, and single-cell eukaryote such as a protozoon.

The term "targeting agent" or "ligand" refers to a molecule which specifically binds to another molecule. For example, an antibody or fragments thereof, aptamers, oligonucleotides, small molecular weight (MW) compounds, carbohydrates, RGD peptides, integrins, receptors or ligands, or any other molecule that can specifically bind to a target molecule. The ligand can be attached to the compound via a linker, conjugated, chemically synthesized, expressed from a nucleic acid sequence, etc.

As used herein, the terms "conjugated," "linked," "attached," "fused" and "tethered," when used with respect to two or more moieties, means that the moieties or domains are physically associated or connected with one another, either directly or via one or more additional moieties that serve as a linking agent, to form a structure that is sufficiently stable so that the moieties remain physically associated under the conditions in which the structure is used, e.g., physiological conditions. The linkage can be based on genetic fusion according to the methods known in the art or can be performed by, e.g., chemical cross-linking. The compounds and targeting agents may be linked by a flexible linker, such as a polypeptide linker. The polypeptide linker can comprise plural, hydrophilic or peptide-bonded amino acids of varying lengths. The term "associated" will be used for the sake of brevity and is meant to include all possible methods of physically associating each compound to a targeting ligand.

"Aptamers" are DNA or RNA molecules that have been selected from random pools based on their ability to bind other molecules. The aptamer binds specifically to a target molecule wherein the nucleic acid molecule has sequence that comprises a sequence recognized by the target molecule in its natural setting. Alternately, an aptamer can be a nucleic acid molecule that binds to a target molecule wherein the target molecule does not naturally bind to a nucleic acid. The target molecule can be any molecule of interest. For example, the aptamer can be used to bind to a ligand-binding domain of a protein, thereby preventing interaction of the naturally occurring ligand with the protein. This is a non-limiting example and those in the art will recognize that other embodiments can be readily generated using techniques generally known in the art (see, e.g., Gold et al., *Annu. Rev. Biochem.* 64:763, 1995; Brody and Gold, *J. Biotechnol.* 74:5, 2000; Sun, *Curr. Opin. Mol. Ther.* 2:100, 2000; Kusser, *J. Biotechnol.* 74:27, 2000; Hermann and Patel, *Science* 287:820, 2000; and Jayasena, *Clinical Chem.* 45:1628, 1999).

The term "antibody" is inclusive of all species, including human and humanized antibodies and the antigenic target, can be from any species. Thus, an antibody, for example, which binds to an antigen "X" can be mouse anti-human X; human anti-human X; humanized anti-human X, goat anti-human X; goat anti-mouse X; rat anti-human X; mouse anti-rat X and the like. The combinations of antibody generated in a certain species against an antigen target, e.g. "X", from another species, or in some instances the same species (for example, in autoimmune or inflammatory response) are limitless and all species are embodied in this invention. The term antibody is used in the broadest sense and includes fully assembled antibodies, monoclonal antibodies (including human, humanized or chimeric antibodies), polyclonal antibodies, multispecific antibodies (e.g., bispecific antibodies), and antibody fragments that can bind antigen (e.g., Fab', F'(ab)$_2$, Fv, single chain antibodies, diabodies), comprising complementarity determining regions (CDRs) of the foregoing as long as they exhibit the desired biological activity.

As used herein, an antibody that "specifically binds" to a target is intended to refer to a targeting ligand, e.g. an antibody that binds to a target with a $K_D$ of $1 \times 10^{-7}$ M or less, more preferably $5 \times 10^{-8}$ M or less, more preferably $3 \times 10^{-8}$ M or less, more preferably $1 \times 10^{-8}$ M or less, even more preferably $5 \times 10^{-9}$ M or less.

The term "does not substantially bind" to a protein or cells, as used herein, means does not bind or does not bind with a high affinity to the protein or cells, i.e. binds to the protein or cells with a $K_D$ of $1 \times 10^{-6}$M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more.

The term "$K_{assoc}$" or "$K_a$," as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$," as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, for example, using a biosensor system such as a BIACORE™ system.

The term "high affinity" for an antibody refers to an antibody having a $K_D$ of $1 \times 10^{-7}$ M or less, more preferably $5 \times 10^{-8}$ M or less, even more preferably $1 \times 10^{-8}$ M or less, even more preferably $5 \times 10^{-9}$ M or less and even more preferably $1 \times 10^{-9}$ M or less for a target antigen. However, "high affinity" binding can vary for other antibody isotypes. For example, "high affinity" binding for an IgM isotype refers to an antibody having a $K^D$ of $10^{-6}$ M or less, more preferably $10^{-7}$ M or less, even more preferably $10^{-8}$ M or less.

The terms, "compound" and "compounds" as used herein refers to a compound encompassed by the generic formulae disclosed herein, any subgenus of those generic formulae, and any forms of the compounds within the generic and sub-generic formulae. Unless specified otherwise, the term further includes the racemates, stereoisomers, and tautomers of the compound or compounds. All stereoisomers are included within the scope of the invention, as pure compounds as well as mixtures thereof. Unless otherwise indicated, individual enantiomers, diastereomers, geometrical isomers, and combinations and mixtures thereof are all encompassed by the present invention. Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Halogen" or "halo" means fluorine, chlorine, bromine or iodine.

"Aliphatic" means a straight- or branched-chain, saturated or unsaturated, non-aromatic hydrocarbon moiety having the specified number of carbon atoms. By way of example, "$C_3$ aliphatic," "$C_1$-$C_5$ aliphatic," or "$C_1$ to $C_5$ aliphatic," the latter two phrases being synonymous for an aliphatic moiety having from 1 to 5 carbon atoms or, where the number of carbon atoms is not explicitly specified, from 1 to 4 carbon atoms (2 to 4 carbons in the instance of unsaturated aliphatic moieties.

The term "alkyl" as used herein refers to a saturated straight, branched, or cyclic, primary, secondary, or tertiary hydrocarbon of typically $C_1$ to $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Alkyl groups can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, or as known to those skilled in the art, for example, as taught in T. W. Greene and P. G. M. Wuts, "Protective Groups in Organic Synthesis," 3$^{rd}$ ed., John Wiley & Sons, 1999, hereby incorporated by reference. By way of illustration, $C_1$-$C_4$ alkyl moieties include, but are not limited to, methyl, ethyl, propyl, isopropyl, isobutyl, t-butyl, 1-butyl, 2-butyl, and the like. The term "alkyl" also includes alkylenes. "Alkylene" means a divalent counterpart of an alkyl group, such as $CH_2CH_2$, $CH_2CH_2CH_2$, and $CH_2CH_2CH_2CH_2$.

The term "alkenyl" as used herein refers to an unsaturated straight, branched, or cyclic, primary, secondary, or tertiary hydrocarbon of typically $C_1$ to $C_{10}$, that has one or more double bonds. The term includes both substituted and unsubstituted alkenyl groups. By way of illustration, $C_2$-$C_4$ alkenyl moieties include, ethenyl (vinyl), 2-propenyl (allyl or prop-2-enyl), cis-1-propenyl, trans-1-propenyl, E- (or Z-) 2-butenyl, 3-butenyl, 1,3-butadienyl (but-1,3-dienyl) and the like. Alkenyl groups can be optionally substituted with one or more moieties comprising: hydroxyl, amino, alkylamino, arylamino, alkoxy, aryloxy, nitro, cyano, sulfonic acid, sulfate, phosphonic acid, phosphate, or phosphonate.

The term "alkynyl" as used herein refers to an unsaturated straight, branched, or cyclic, primary, secondary, or tertiary hydrocarbon of typically $C_1$ to $C_{10}$, that has one or more triple bonds. By way of illustration, $C_2$-$C_4$ alkynyl groups include ethynyl (acetylenyl), propargyl (prop-2-ynyl), 1-propynyl, but-2-ynyl, and the like. The term includes both substituted and unsubstituted alkynyl groups. Alkynyl groups can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate. The terms "alkylamino" or "arylamino" as used herein refer to an amino group that has one or two alkyl or aryl substituents, respectively.

The term "aryl" as used herein refers to phenyl, biphenyl, or naphthyl. The rings in the ring system may be fused to each other (as in naphthyl) or bonded to each other (as in biphenyl) and may be fused or bonded to non-aromatic rings (as in indanyl or cyclohexylphenyl). By way of further illustration, aryl moieties include, but are not limited to, phenyl, naphthyl, tetrahydronaphthyl, indanyl, biphenyl, phenanthryl, anthracenyl, and acenaphthyl. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate. "Arylene" means a divalent counterpart of an aryl group, for example 1,2-phenylene, 1,3-phenylene, or 1,4-phenylene. The term includes both substituted and unsubstituted moieties.

The term "alkaryl" as used herein refers to an alkyl group with an aryl substituent.

The term "acyl" as used herein refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen (F, Cl, Br, I), $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group.

As used herein, the term "alkoxy" refers to an optionally substituted straight or branched chain alkyl —O— group wherein alkyl is as previously defined.

For example, $C_{1-10}$ alkoxy means a straight or branched alkoxy containing at least 1, and at most 10, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy. A $C_{1-4}$ alkoxy group is preferred, for example methoxy, ethoxy, propoxy, prop-2-oxy, butoxy, but-2-oxy or 2-methylprop-2-oxy. As used herein, the term "aryloxy" refers to an optionally substituted aryl-O-group wherein aryl is as previously defined. Exemplary aryloxy groups include, but are not limited to, phenoxy (phenyl-O—).

As used herein, the term "heteroaryl" refers to an optionally substituted aryl ring system wherein, in at least one of the rings, one or more of the carbon atom ring members is independently replaced by a heteroatom group selected from the group consisting of S, O, N, where the N and S optionally may be oxidized and the N optionally may be quaternized, and NH, or NR wherein aryl is as previously defined and R is an optional substituent as defined herein. Heteroaryl groups having a total of from about 5 to about 14 carbon atom ring members and heteroatom ring members (and all combinations and subcombinations of ranges and specific numbers of carbon and heteroatom ring members) are preferred. Heteroaryl groups having a total of from about 5 to about 10 carbon atom ring members and heteroatom ring members (and all combinations and subcombinations of ranges and specific numbers of carbon and heteroatom ring members) are more preferred. Exemplary heteroaryl groups include, but are not limited to, pyrryl, furyl, pyridyl, pyridine-N-oxide, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Heteroaryl may be attached to the rest of the molecule via a carbon or a heteroatom. "Heteroarylene" means a divalent counterpart of an aryl group.

Where it is indicated that a moiety may be substituted, such as by use of "unsubstituted or substituted" or "optionally substituted" phrasing as in "unsubstituted or substituted $C_1$-$C_5$ alkyl" or "optionally substituted heteroaryl," such moiety may have one or more independently selected substituents, e.g. one to five in number, one or two in number, etc. Substituents and substitution patterns can be selected by one of ordinary skill in the art, having regard for the moiety to which the substituent is attached, to provide compounds that are chemically stable and that can be synthesized by techniques known in the art as well as the methods set forth herein.

As used herein, the term "heteroarylalkyl" refers to an optionally substituted ring system comprising an alkyl radical bearing a heteroaryl substituent, each as defined above, having at least 6 carbon atoms, for example, from about 6 to about 25 carbon atoms (and all combinations and subcombinations of ranges and specific numbers of carbon atoms therein).

As used herein, the term "heterocycloalkyl," "heterocyclic ring" and "heterocyclyl" each refer to an optionally substituted ring system composed of a cycloalkyl radical wherein, in at least one of the rings, one or more of the carbon atom ring members is independently replaced by a heteroatom group selected from the group consisting of O, S, N, and NH, or NR wherein cycloalkyl is as previously defined and R is an optional substituent as defined herein. Heterocycloalkyl ring systems having a total of from about 3 to about 14 carbon atom ring members and heteroatom ring members (and all combinations and subcombinations of ranges and specific numbers of carbon and heteroatom ring members) are preferred, more preferably from about 3 to about 10 ring atom members.

"Cycloaliphatic" means a saturated or unsaturated, non-aromatic hydrocarbon moiety having from 1 to 3 rings, each ring having from 3 to 8 carbon atoms. "Cycloalkyl" means a cycloaliphatic moiety in which each ring is saturated. "Cyclo-alkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl. "Cycloalkylene" means a divalent counterpart of a cycloalkyl group.

"Heterocycloaliphatic" means a cycloaliphatic moiety wherein, in at least one ring thereof, up to three carbons have been replaced with a heteroatom independently selected from N, O, or S, where the N and S optionally may be oxidized and the N optionally may be quaternized. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like. "Heterocycloalkylene" means a divalent counterpart of a heterocycloalkyl group.

"Alkoxy," "aryloxy," "alkylthio," and "arylthio" mean —O(alkyl), —O(aryl), —S(alkyl), and —S(aryl), respectively. Examples are methoxy, phenoxy, methylthio, and phenylthio, respectively.

"Arylalkyl," (heterocycloaliphatic)alkyl," "arylalkenyl," "arylalkynyl," "biarylalkyl," and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl," "alkenylcycloalkyl," and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl," "haloalkyl," "alkylaryl," "cyanoaryl," and the like mean an alkyl, aryl, etc., moiety, as the case may be, substituted with one or more of the identified substituent (hydroxyl, halo, etc., as the case may be).

Typically, substituted chemical moieties include one or more substituents that replace hydrogen. Exemplary substituents include, for example, halo (e.g., F, Cl, Br, I), alkyl, cycloalkyl, alkylcycloalkyl, alkenyl, alkynyl, haloalkyl including trifluoroalkyl, aralkyl, aryl, heteroaryl, heteroarylalkyl, spiroalkyl, heterocyclyl, heterocycloalkyl, hydroxyl (—OH), alkoxyl, aryloxyl, aralkoxyl, nitro (—NO$_2$), cyano (—CN), amino (—NH$_2$), N-substituted amino (—NHR"), N,N-disubstituted amino (—N(R")R"), carboxyl (—COOH), —C(=O)R", —OR", —C(=O)OR", —C(=O)NHSO$_2$R", —NHC(=O)R", aminocarbonyl (—C(=O)NH$_2$), N-substituted aminocarbonyl (—C(=O)NHR"), N,N-disubstituted aminocarbonyl (—C(=O)N(R")R"), thiolato (SR"), sulfonic acid and its esters (—SO$_3$R"), phosphonic acid and its mono-ester (—P(=O)(OR")(OH) and di-esters (—P(=O)(OR")(OR"), —S(=O)$_2$R", —S(=O)$_2$NH$_2$, —S(=O)$_2$NHR", —S(=O)$_2$NR"R", —SO$_2$NHC(=O)R", —NHS(=O)$_2$R", —NR"S(=O)$_2$R", —CF$_3$, —CF$_2$CF$_3$, —NHC(=O)NHR", —NHC(=O)NR"R", —NR"C(=O)NHR", —NR"C(=O)NR"R", —NR"C(=O)R" and the like. In relation to the aforementioned substituents, each moiety "R" can be, independently, any of H, alkyl, cycloalkyl, alkenyl, aryl, aralkyl, heteroaryl, or heterocycloalkyl, or when (R"(R")) is attached to a nitrogen atom, R" and R" can be taken together with the nitrogen atom to which they are attached to form a 4- to 8-membered nitrogen heterocycle, wherein the heterocycloalkyl ring is optionally interrupted by one or more additional —O—, —S—, —SO, —SO$_2$—, —NH—, —N(alkyl)-, or —N(aryl)- groups, for example. In certain embodiments, chemical moieties are substituted by at least one optional substituent, such as those provided hereinabove. In the present invention, when chemical moieties are substituted with optional substituents, the optional substituents are not further substituted unless otherwise stated. For example, when $R^1$ is an alkyl moiety, it is optionally substituted, based on the definition of "alkyl" as set forth herein. In some embodiments, when $R^1$ is alkyl substituted with optional aryl, the optional aryl substituent is not further substituted. The term "optionally substituted" means that group in question may be unsubstituted or it may be substituted one or several times, such as 1 to 3 times or 1 to 5 times. For example, an alkyl group that is "optionally substituted" with 1 to 5 chloro atoms, may be unsubstituted, or it may contain 1, 2, 3, 4, or 5 chlorine atoms.

By way of illustration, substituents include, but are not limited to, alkyl (especially methyl or ethyl), alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —OCF$_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl) 2, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(=O)alkyl, —S(cycloalkyl), —SO$_2$(alkyl), —SO$_2$NH$_2$, —SO$_2$NH (alkyl), and —SO$_2$N(alkyl)$_2$. More preferred substituents are halo, hydroxyl, cyano, nitro, alkoxy, —O(aryl), =O, =NOH, =NO(alkyl), —OC(=O)(alkyl), —OC(=O)O (alkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are phenyl, cyano, halo, hydroxyl, nitro, C$_1$-C$_4$alkyoxy, O(C$_2$-C$_4$ alkylene)OH, and O(C$_2$-C$_4$ alkylene)halo.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O(hydroxyalkyl), —O(haloalkyl), —O(aryl), —O(cycloalkyl), —O(heterocycloalkyl), alkylthio, arylthio, —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. In some embodiments, substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH(alkyl), —OC(=O)N(alkyl)$_2$, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. In some embodiments, substituents are C$_1$-C$_4$ alkyl, cyano, nitro, halo, and C$_1$-C$_4$ alkoxy.

When any variable occurs more than one time in any constituent or formula for a compound, its definition at each occurrence is independent of its definition at every other occurrence. Thus, for example, if the R$^5$ group is shown to be substituted with 0-2 substituents, then said group may optionally be substituted with up to two substituents and each substituents is selected independently from the definition of optionally substituted defined above. Also, combinations of substituents and/or variables are permissible only if such combinations result in stable compounds.

When a bond to a substituent is shown to cross a bond connecting two atoms in a ring, then such substituent may be bonded to any atom on the ring having an attached hydrogen atom. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The term "amino acid" as used herein refers to naturally occurring and synthetic α, β, γ, and δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl; glutaminyl, aspartoyl, glutaroyl, lysinyl, argininyl, histidinyl, β-alanyl, β-valinyl, β-leucinyl, β-isoleucinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. When the term amino acid is used, it is considered to be a specific and independent disclosure of each of the esters of α, β, γ, and δ glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine in the D and L-configurations.

A "label" or a "detectable label" is a composition detectable by spectroscopic, photochemical, biochemical, immunochemical, or chemical means. For example, useful labels include radio labeled molecules fluorophores, radiochemical, luminescent compounds, electron-dense reagents, enzymes (e.g., as commonly used in an ELISA), biotin, radioactive compounds, non-radioactive compounds, digoxigenin, or haptens and proteins which can be made detectable, e.g., by incorporating a label into the peptide.

The term "radiochemical" is intended to encompass any organic, inorganic or organometallic compound comprising a covalently-attached radioactive isotope, any inorganic radioactive ionic solution (e.g., Na[$^{18}$F]F ionic solution), or any radioactive gas (e.g., [$^{11}$C]CO$_2$), particularly including radioactive molecular imaging probes intended for administration to a patient (e.g., by inhalation, ingestion, or intravenous injection) for tissue imaging purposes, which are also referred to in the art as radiopharmaceuticals, radiotracers, or radioligands. The compounds could also be readily adapted for synthesis of any radioactive compound comprising a radionuclide, including radiochemicals useful in other imaging systems, such as single photon emission computed tomography (SPECT).

Another aspect is a radiolabeled compound of any of the formulae delineated herein. Such compounds have one or more radioactive atoms (e.g., $^3$H, $^2$H, $^{14}$C, $^{13}$C, $^{35}$S, $^{32}$P, $^{125}$I, $^{131}$I) introduced into the compound. Such compounds are useful for drug metabolism studies and diagnostics, as well as therapeutic applications.

Another aspect includes non-radioactive labeled compounds of any of the formulae delineated therein. These include fluorescent molecules, dyes, optical imaging agents, and the like. The term "optical imaging agent" refers to molecules that have wavelength emission greater than 400 nm and below 1200 nm. Examples of optical imaging agents are Alex Fluor, BODIPY, Nile Blue, COB, rhodamine, Oregon green, fluorescein and acridine.

As used herein, "pharmaceutical salts" include, but are not limited to, mineral or organic acid salts of basic residues such as amines; alkali or organic salts of acidic residues such as carboxylic acids. Preferably the salts are made using an organic or inorganic acid. These preferred acid salts are chlorides, bromides, sulfates, nitrates, phosphates, sulfonates, formates, tartrates, maleates, malates, citrates, benzoates, salicylates, ascorbates, and the like. The most preferred salt is the hydrochloride salt.

As used herein, a "pharmaceutically acceptable" component/carrier etc is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

The terms "subject", "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates. Patients in need of therapy comprise those at risk of developing a certain condition, disease or disorder (e.g. due to genetic, environmental or physical attributes, such as for example, obesity). Patients in need of therapy also include those afflicted with a condition, disease or disorder. The diseases or disorders comprise, for example: autoimmune diseases, cancer, inflammatory diseases, neurological diseases or disorders, neuroinflammatory diseases or disorders, cardiovascular disease, obesity, diseases or disorders caused by infectious agents such as, for example, viruses, bacteria, fungi, prions, or parasites.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1-minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. Accordingly, "treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (2) inhibiting the state, disorder or condition, i.e., arresting, reducing or delaying the development of the disease or a relapse thereof (in case of maintenance treatment) or at least one clinical or subclinical symptom thereof; or (3) relieving the disease, i.e., causing regression of the state, disorder or condition or at least one of its clinical or subclinical symptoms. The benefit to an individual to be treated is either statistically significant or at least perceptible to the patient or to the physician.

Compounds

The enediynes exert their effects by DNA double-strand breaks (DSBs), interstrand crosslinks (ICLs), or both. The exquisite potency and mechanisms of action of these molecules make them ideal payloads for anticancer antibody-drug conjugates (ADCs). However, among the 60+ ADCs currently in development, the majority of them use one of the five available drugs, and the ADC field is in critical need of new, highly potent cytotoxic payloads ($IC_{50s}$ at 1 nM to 10 pM), with improved physical, chemical, and biological properties. Thus, new enediynes bearing these properties would be extremely valuable assets in the development of safer, more effective ADCs.

Only 11 enediyne natural products are currently known. A high-throughput real-time PCR was developed by the inventor, B. Shen (U.S. Ser. No. 62/016,292; incorporated by reference herein in its entirety) as a method to prioritize strains for natural product discovery. This method was adapted to identify strains that are of a high likelihood to encode enediyne biosynthesis. Detailed follow-up genome sequencing, genetic manipulation, and fermentation optimization of the most promising strains are likely to yield new enediynes, some of which could be realistically developed into anticancer ADC payload leads.

The enediynes present an outstanding opportunity to (i) decipher the genetic and biochemical basis for the biosynthesis of complex natural products, (ii) explore ways to make novel analogues by manipulating genes governing their biosynthesis, and (iii) discover new enediyne natural products by mining microbial genomes for the trademark enediyne biosynthetic machineries. Enediyne natural products are very scarce and only 11 enediynes are structurally characterized to date, with an additional four proposed to be isolated in the cyclo-aromatized form.

The enediynes are classified into two subcategories according to the size of the enediyne core structures. Members of the 9-membered enediyne core subcategory are chromoproteins, commonly consisting of an apoprotein and the enediyne chromophore, including neocarzinostatin (NCS) (Edo, K. et al. *Tetrahedron Lett.* 1985, 26, 331-340), C-1027 (Zhen, Y.-S. et al. *J. Antibiot.* 1989, 42, 1294-1298; Yoshida, K. et al. *Tetrahedron Lett.* 1993, 34, 2637-2640; Minami, Y. et al. *Tetrahedron Lett.* 1993, 34, 2633-2636; Iida, K. et al. *Tetrahedron Lett.* 1996, 37, 4997-5000; Otani, T. et al. *J. Antibiot.* 1999, 52, 415-421), kedarcidin (KED) (Leet, J. E. et al. *J. Am. Chem. Soc.* 1992, 114, 7946-7948; Kawata, S. et al. *J. Am. Chem. Soc.* 1997, 119, 12012-12013; Ren, F. et al. *J. Am. Chem. Soc.* 2007, 129, 5381-5383), maduropeptin (MDP) (Schroeder, D. R. et al. *J. Am. Chem. Soc.* 1994, 116, 9351-9352; Komano, K. et al. *J. Am. Chem. Soc.* 2009, 131, 12072-12073), N1999A2 (Ando, T. et al. *Tetrahedron Lett.* 1998, 39, 6495-6498; Kobayashi, S. et al. *J. Am. Chem. Soc.* 2001, 12, 11294-11295), the sporolides (SPO) (Buchanan, G. O. et al. *Org. Lett.* 2005, 7, 2731-2734; McGlinchey, R. P. et al. *J. Am. Chem. Soc.* 2008, 130, 2406-2407), the cyanosporasides (CYA and CYN) (Oh, D.-C. et al. *Org. Lett.* 2006, 8, 1021-1024; Lane, A. L. et al.

*J. Am. Chem. Soc.* 2013, 135, 4171-4174), and the fijiolides (Nam, S.-J. et al. *J. Nat. Prod.* 2010, 73, 1080-1086), with the latter four isolated in the absence of an apoprotein. Members of the 10-membered enediyne core subcategory are discrete small molecules, including the calicheamicins (CAL) (Lee, M. D. et al. *J. Am. Chem. Soc.* 1987, 109, 3464-3466; Lee, M. D. et al. *J. Am. Chem. Soc.* 1987, 109, 3466-3468), DYN (Konishi, M. et al. *J. Antibiot.* 1989, 1449-1452; Myers, A. G. et al. *Chem. Biol.* 1995, 2, 33-43), the esperamicins (ESP) (Golik, J. et al. *J. Am. Chem. Soc.* 1987, 109, 3461-3462; Golik, J. et al. *J. Am. Chem. Soc.* 1987, 109, 3462-3464), namenamicin (McDonald, L. A.; et al. *J. Am. Chem. Soc.* 1996, 118, 10898-10899), dynemicin (DYN), and uncialamycin (UCM) (Davies, J. et al. *Org. Lett.* 2005, 7, 5233-5236). All enediynes contain a unit consisting of two acetylenic groups conjugated to a double bond or incipient double bond within the 9- or 10-membered carbacycle. As a consequence of this structural feature, these compounds share a common mode of action. Electronic rearrangement (Bergman or Myers-Saito rearrangement) of the enediyne carbacycle produces a transient benzenoid diradical. When positioned within the minor groove of DNA, the diradical abstracts hydrogen atoms from the deoxyribose backbone of duplex DNA; the DNA-centered radicals can then cause ICLs, react with molecular oxygen leading ultimately to DNA DSBs, or both.

Strain Prioritization for Novel Natural Product Discovery.

Traditional microbial natural product discovery programs start from fermenting each strain individually, often in multiple media, followed by preparation of crude extracts. There are two primary approaches to search for novel natural products from extracts: bioassay-guided fractionation and chemical profiling of compounds possessing unique structural novelty. In both cases, a molecule of interest must be produced in sufficient amounts in order to permit isolation and characterization on a reasonable timeframe. The ultimate success in discovering a new natural product typically requires three principal steps: de-replication of known compounds to avoid duplication of effort, isolation of the targeted molecules from a highly complex matrix, and structural elucidation of the purified natural product. This tedious and laborious traditional process could be significantly shortened if the biosynthetic potential of a strain collection is known in advance. Resources could then be devoted preferentially to interrogate only the strains that hold the highest promise in producing novel natural products.

Complementary to traditional approaches, the progress made in the last two decades in connecting natural products to the genes that encode their biosynthesis has fundamentally changed the landscape of natural products research and sparked the emergence of a suite of contemporary approaches to natural product discovery. Thus, genes have become as important as chemistry in categorizing known natural products and identifying new ones. Advances in microbial genomics have unequivocally demonstrated that ~90% of the natural product biosynthetic capacity of even the workhorse producers, the Actinobacteria is missing. To gain access to this untapped reservoir of potentially new natural products, two principal strategies have been applied to induce these "cryptic biosynthetic pathways".

The so-called 'epigenetic'-related approaches include challenging the microorganisms through culture conditions, nutritional or environmental factors, external cues, and stress, as well as, exploiting interspecies crosstalk. The genomics-based approaches include mining the genomes to predict metabolite structures, engineering the pathways by manipulating global and/or pathway-specific regulators, and expressing the cryptic pathways in selected heterologous hosts. While each of the various approaches has different strengths and weaknesses, they have been successful in yielding cryptic natural products but only on a case-by-case basis and are far from being of practical use for natural product discovery. Thus, in spite of the rapid advances in DNA sequencing technologies and bioinformatics, it is still unlikely to sequence and annotate all strains within a large collection as a practical means to discover new natural products.

Adapting the recently reported high-throughput real-time PCR method for strain prioritization (Hindra et al. *J. Nat. Prod.* 2014, 77, 2296-2303; Shen, B. et al. *Bioorg. Med. Chem. Lett.* 2015, 25, 9-15; Rudolf, J. D. et al. *J. Ind. Microbiol. Biotechnol,* 2015, early edition, DOI 10.1007/s10295-015-1671-0), an innovative genome survey strategy was developed to rapidly identify strains, from an *Actinomycetale* collection, that are of high likelihood to produce enediyne natural products. It was found that these strains are the most prolific enediyne producers. A genome survey of 3,500 strains was completed from this laboratory's *Actinomycetale* collection, identifying 94 potential enediyne producers (hits). It was demonstrated, by genome sequencing, that these hits were true enediyne producers, containing gene clusters that are distinct to enediyne clusters and, by genetic manipulation and fermentation optimization, that the most promising hits can be activated to produce new enediyne natural products.

Genetic Manipulation of Actinomycetales and *Streptomyces* to Activate Enediyne Biosynthesis and Production.

There are minimally four requirements for implementing metabolic pathway engineering strategies to natural product discovery and structural diversity. These are: (i) the gene clusters encoding the production of a particular natural product or family of natural products, (ii) genetic and biochemical characterizations of the targeted biosynthetic machinery to a degree that combinatorial biosynthesis principles can be rationally applied to engineer the novel analogues, (iii) expedient genetic systems for in vivo manipulation of genes governing the production of the target molecules in either native producers or heterologous hosts, and (iv) production of the natural products or engineered analogues to levels that are sufficient for isolation and characterization.

Although each of these requirements is essential, establishing an expedient genetic system for in vivo manipulation of the targeted biosynthetic machinery is of paramount importance. Thus, an opportunity for innovation in manipulating enediyne biosynthesis is the selection of the producers that are compatible with the expedient technologies and tools of recombinant DNA work in *Streptomyces* species and related organisms that have been developed in the past two decades. The CAL, DYN, and ESP (partial) clusters were cloned from *M. echinospora, M. chersina,* and *A. verrucosospora,* respectively, and genetic manipulations in *Micromonospora* and *Actinomadura* are notoriously difficult. As a result, the ESP cluster is incomplete, and the boundaries of both the CAL and DYN clusters have yet to be determined experimentally. In contrast, biosynthesis and engineering of C-1027, NCS, and UCM have been greatly facilitated by the expedient genetic systems in *S. globisporus, S. carzinostaticus,* and *S. uncialis,* respectively. Accordingly, *Streptomyces* was biased in the *Actinomycetale* strain collection, and this selection overcomes the current challenges of, and meeting future objectives for, enediyne discovery, biosynthesis, and engineering in their native producers.

The availability of four 9-membered (C-1027, NCS, MDP, KED) and four 10-membered [CAL, ESP (partial), DYN, and UCM] enediyne gene clusters, as well as the three additional clusters encoding the biosynthesis of the cycloaromatized enediyne natural products of sporolides and cyanosporasides. By comparing the gene clusters between the 9- and 10-membered enediynes, a unified model was formulated for the enediyne PKS cassette to catalyze the formation of both 9- and 10-membered enediyne cores, on which the current genome survey strategy for enediyne discovery was developed. By comparing metabolite profiles of the enediyne native producers, selected mutant strains, and recombinant strains expressing selected genes within the enediyne PKS cassette, a metabolomics method was established to follow the biosynthesis of heptaene as a sensitive phenotypic indicator for enediyne production. By manipulating the regulatory genes within the C-1027 biosynthetic gene cluster, C-1027 production was significantly improved. Application of the comparative genomics approach to analyze the new enediyne clusters promises to reveal equally informative insights into their structures, biosynthesis, and regulations. The fact that most of the new enediyne producers discovered are of *Streptomyces* origin ensures that the extensive genetic tools available in *Streptomyces* can be readily applied to facilitate the discovery and production of the new enediynes in the native producers.

Preparation of complex natural products such as the enediynes and their analogues by total synthesis poses a monumental challenge to synthetic chemists. Combinatorial biosynthesis offers an excellent alternative to produce natural products and their analogues biosynthetically. Target metabolites can be produced by recombinant organisms that are amenable to large-scale fermentation.

Application of combinatorial biosynthetic strategies to address titer improvement, production bottlenecks, production of selected metabolites, optimization of natural product leads, and generation of natural product diversity have all been demonstrated. Application of combinatorial biosynthesis strategies to the biosynthetic machineries in the new enediyne producers from our *Actinomycetale* collection promises to enable the discovery and production of novel enediynes.

Natural Products as Drug Leads and Drugs.

Natural products remain the best source of new drug leads and drugs, particularly for anticancer drugs. Natural products possess enormous structural and chemical diversity unsurpassed by any synthetic libraries and are evolutionarily optimized as drug-like molecules. The history of medicine is full of success stories about natural product inspired drug discovery and semi-synthetic modifications of natural product leads into marketable drugs. While the rich functionalities of natural products have been credited for their great potency and selectivity, they also present great challenges to practical synthesis. Re-supply of natural products is often problematic as exemplified by natural products from slow-growing plants or other species at the verge of extinction due to overharvesting and ecosystem destruction. In contrast, microbial natural products always enjoy the feasibility of reliable supply by fermentation, allowing large-scale production for follow up experiments, clinical trials, and ultimate commercialization.

Engineering Cellular Biosynthetic Machinery for the Production of Novel Analogues:

Manipulations of gene encoding natural product biosynthesis for natural product structural diversity have now been well demonstrated. For example, the cloned tiancimycin biosynthetic gene cluster from S. sp. CB03234 sets the stage to engineer the tiancimycin biosynthetic machinery for the production of novel analogues. Comparison and contrasting the genes encoding the enediyne core biosynthesis between tiancimycin and other enediyne biosynthetic pathways provide outstanding opportunities to produce tiancimycin analogues with altered enediyne core structures.

In some embodiments, a method of producing a novel enediyne compound or an analogue of an enediyne compound comprises: (i) targeting the gene cluster encoding the production of the natural product or the family of natural products, (ii) genetic and biochemical characterizations of the biosynthetic machinery for the targeted natural products to a degree that the combinatorial biosynthesis principles can be rationally applied to engineer the novel analogues, (iii) expedient genetic systems for in vivo manipulation of genes governing the production of the target molecules in their native producers or heterologous hosts, and (iv) production of the natural products or their engineered analogues to levels that are appropriate for detection, isolation, and structural and biological characterization. Accordingly, in embodiments, engineering or mutating the genes encoding the tailoring steps of tiancimycin biosynthesis, such as the O-methyltransferase and cytochrome $P_{450}$ monooxygenase for the anthraquinone moiety, produces novel tiancimycin analogues with altered functional groups, thereby modulating their biological activities or providing reactive chemical handles for further modification by medicinal chemistry, as exemplified by the S. sp. CB03234 ΔtnmH mutant strain that produces the designer enediyne tiancimycin C.

In one embodiment, a method of producing a novel enediyne compound comprises mutating target genes of an enediyne producing cell, and screening for enediyne compounds. Alternatively, a method of producing a novel enediyne compound comprises mutating target genes or target sequences of an enediyne producing cell, cloning the mutated sequences into an expression vector; transfecting a host cell with the expression vector comprising one or more mutated nucleic acid sequences and screening for novel enediyne compounds. In another embodiment, a method of producing a novel enediyne comprises cloning a gene of interest from an enediyne producing cell, mutating the gene of interest and transfecting a host with an expression vector containing the mutated gene(s); and, screening for enediyne compounds. Methods of mutating genes are well-known in the art. Screening for compounds can be conducted as described in the examples section which follows and in further detail as described in U.S. provisional patent application, U.S. Ser. No. 62/016,292 (incorporated by reference herein in its entirety). The high-throughput real-time PCR was developed by the inventor, B. Shen as a method to prioritize strains for natural product discovery. This method was adapted to identify strains that are of a high likelihood to encode enediyne biosynthesis.

In one aspect, the invention provides for the identification of microbial natural products as novel anticancer drug leads so that the most promising drug candidates can be reliably produced by large-scale fermentation.

In another aspect the invention provides for the use of the enediyne family of natural products as payload candidates of anticancer ADCs.

In another aspect, the invention provides for the development of a genome survey strategy to rapidly identify the most promising enediyne producers that hold the highest potential in producing novel enediynes.

In another aspect, the invention provides a multifaceted approach combining genomics, bioinformatics, metabolic pathway engineering strategies and methods, medium and fermentation optimization, and metabolomics to activate the biosynthesis for production, isolation, and subsequent structural characterization, of the novel enediyne natural products.

In an embodiment, a compound comprises a structure represented by formula I, or a pharmaceutically acceptable salt thereof:

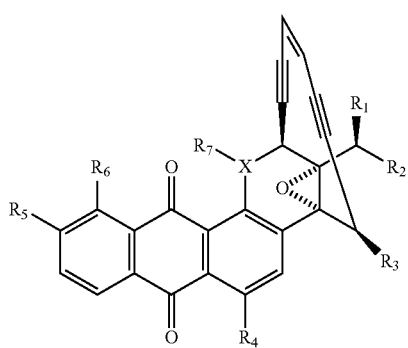

(I)

wherein, $R_1$, $R_2$, $R_3$, $R_4$, $R_5$, $R_6$ and $R_7$ are each independently H, O, OH, F, Cl, Br, $CH_3$, R', OR', $NH_2$, NHR', $NR'_2$, SH, SR', C(O)R, $RCO_2R'$, halogen, alkyl, heteroatom substituted alkyl, unsaturated alkyl, polyunsaturated alkyl, aryl, heteroaryl, cycloalkyl, alkenyl, alkyryl, acyl, alkoxy, heteroarylalkyl, heterocycloalkyl, cycloaliphatic, heterocycloaliphatic, arylalkyl, heteroatom-substituted analogs, optionally substituted $C_1$-$C_{10}$ alkyl, optionally substituted $C_1$-$C_{10}$ alkenyl, optionally substituted $C_1$-$C_{10}$ alkynyl, optionally substituted aryl, optionally substituted alkaryl, optionally substituted alkoxyl, optionally substituted heteroaryl, optionally substituted arylalkoxyl, optionally substituted acyl, optionally substituted arylalkyl, (heterocycloaliphatic) alkyl, optionally substituted arylalkenyl, optionally substituted arylalkynyl, optionally substituted biarylalkyl, alkylaryl, alkenylcycloalkyl, hydroxyalkyl, haloalkyl, alkylaryl, cyanoaryl, substituted with one or more of the identified substituent (hydroxyl, halo, etc., as the case may be), OH, OR', $NH_2$, NHR', $NR'_2$, SH, SR', C(O)R', wherein R' comprises H, halogen, optionally substituted $C_1$-$C_{10}$ alkyl, optionally substituted $C_1$-$C_{10}$ alkenyl, optionally substituted $C_1$-$C_{10}$ alkynyl, optionally substituted aryl, optionally substituted alkaryl, or optionally substituted acyl, alkyl, alkenyl, alkynyl, aryl, heteroaryl, cycloaliphatic, heterocycloaliphatic, halo especially fluoro), haloalkyl (especially trifluoromethyl), hydroxyl, hydroxyalkyl, cyano, nitro, alkoxy, —O(hydroxyalkyl), —O(haloalkyl) (especially —$OCF_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —$CO_2H$, —C(=O)NHOH, —C(=O)O(alkyl), —C(=O)O(hydroxyalkyl), —C(=O)$NH_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)$NH_2$, —OC(=O)NH(alkyl), —OC(=O)N(alkyl)$_2$, azido, —$NH_2$, —NH(alkyl), —N(alkyl)$_2$, —NH(aryl), —NH(hydroxyalkyl), —NHC(=O)(alkyl), —NHC(=O)H, —NHC(=O)$NH_2$, —NHC(=O)NH(alkyl), —NHC(=O)N(alkyl)$_2$, —NHC(=NH)$NH_2$, —$OSO_2$(alkyl), —SH, —S(alkyl), —S(aryl), —S(cycloalkyl), —S(=O)alkyl, —$SO_2$(alkyl), —$SO_2NH_2$, —$SO_2$NH(alkyl), —$SO_2$N(alkyl)$_2$, and the like.

Where the moiety being substituted is an aliphatic moiety, substituents comprise aryl, heteroaryl, cycloaliphatic, heterocycloaliphatic, halo, hydroxyl, cyano, nitro, alkoxy, —O(hydroxyalkyl), —O(haloalkyl), —O(cycloalkyl), O(heterocycloalkyl), —O(aryl), alkylthio, arylthio, =O, =NH, =N(alkyl), =NOH, =NO(alkyl), —$CO_2H$, —C(=O)NHOH, —C(=O)O(alkyl), —C(=O)O(hydroxyalkyl), —C(=O)$NH_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)$NH_2$, —OC(=O)NH(alkyl), —OC(=O)N(alkyl)$_2$, azido, —$NH_2$, —NH(alkyl), —N(alkyl)$_2$, —NH(aryl), —NH(hydroxyalkyl), —NHC(=O)(alkyl), —NHC(=O)H, —NHC(=O)$NH_2$, —NHC(=O)NH(alkyl), —NHC(=O)N(alkyl)$_2$, —NHC(=NH)$NH_2$, —$OSO_2$(alkyl), —SH, —S(alkyl), —S(aryl), —S(=O)alkyl, —S(cycloalkyl), —$SO_2$(alkyl), —$SO_2NH_2$, —$SO_2$NH(alkyl), and —$SO_2$N(alkyl)$_2$. Some preferred substituents are halo, hydroxyl, cyano, nitro, alkoxy, —O(aryl), =O, =NOH, =NO(alkyl), —OC(=O)(alkyl), —OC(=O)O(alkyl), —OC(=O)$NH_2$, —OC(=O)NH(alkyl), —OC(=O)N(alkyl)$_2$, azido, —$NH_2$, —NH(alkyl), —N(alkyl)$_2$, —NH(aryl), —NHC(=O)(alkyl), —NHC(=O)H, —NHC(=O)$NH_2$, —NHC(=O)NH(alkyl), —NHC(=O)N(alkyl)$_2$, and —NHC(=NH)$NH_2$. Other preferred substitutions are phenyl, cyano, halo, hydroxyl, nitro, $C_1$-$C_4$ alkyoxy, O($C_2$-$C_4$ alkylene)OH, and O($C_2$-$C_4$ alkylene)halo. Where the moiety being substituted is a cycloaliphatic, heterocycloaliphatic, aryl, or heteroaryl moiety, substituents comprise alkyl, alkenyl, alkynyl, halo, haloalkyl, hydroxyl, hydroxyalkyl, cyano, nitro, alkoxy, —O(hydroxyalkyl), —O(haloalkyl), —O(aryl), —O(cycloalkyl), —O(heterocycloalkyl), alkylthio, arylthio, —C(=O)(alkyl), —C(=O)H, —$CO_2H$, —C(=O)NHOH, —C(=O)O(alkyl), —C(=O)O(hydroxyalkyl), —C(=O)$NH_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)$NH_2$, —OC(=O)NH(alkyl), —OC(=O)N(alkyl)$_2$, azido, —$NH_2$, —NH(alkyl), —N(alkyl)$_2$, —NH(aryl), —NH(hydroxyalkyl), —NHC(=O)(alkyl), —NHC(=O)H, —NHC(=O)$NH_2$, —NHC(=O)NH(alkyl), —NHC(=O)N(alkyl)$_2$, —NHC(=NH)$NH_2$, —$OSO_2$(alkyl), —SH, —S(alkyl), —S(aryl), —S(cycloalkyl), —S(=O)alkyl, —$SO_2$(alkyl), —$SO_2NH_2$, —$SO_2$NH(alkyl), and —$SO_2$N(alkyl)$_2$. In some embodiments, substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —$CO_2H$, —C(=O)NHOH, —C(=O)O(alkyl), —C(=O)O(hydroxyalkyl), —C(=O)$NH_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH(alkyl), —OC(=O)N(alkyl)$_2$, —$NH_2$, —NH(alkyl), —N(alkyl)$_2$, —NH(aryl), —NHC(=O)(alkyl), —NHC(=O)H, —NHC(=O)$NH_2$, —NHC(=O)NH(alkyl), —NHC(=O)N(alkyl)$_2$, and —NHC(=NH)$NH_2$. In some embodiments, substituents are $C_1$-$C_4$ alkyl, cyano, nitro, halo, and $C_1$-$C_4$ alkoxy or an amino acid side chain, along with any stereoisomeric, tautomeric, or polymeric form thereof.

In other embodiments, the compound having the structure represented by formula (I) is conjugated to a targeting ligand wherein the targeting ligand specifically binds to a target molecule comprising tumor antigens, antigens or markers associated with a disease or infectious organism. Various diseases or conditions include, but are not limited to those categorized in standard textbooks of medicine including, without limitation, textbooks of nutrition, allopathic, homeopathic, and osteopathic medicine. In certain aspects of this invention, the disease or condition comprises the types of diseases listed in standard texts such as Harrison's Principles of Internal Medicine, 14$^{th}$ Edition (Fauci et al, Eds., McGraw Hill, 1997), or Robbins Pathologic Basis of Disease, 6$^{th}$ Edition (Cotran et al, Ed. W B Saunders Co., 1998), or the Diagnostic and Statistical Manual of Mental Disorders: DSM-IV, 4$^{th}$ Edition, (American Psychiatric Press, 1994), or other text books, which are incorporated herein in their entirety.

In another embodiment, a composition comprises an enediyne compound, analogs or derivatives thereof conjugated to a targeting ligand. In an embodiment, the enediyne compound comprises a structure represented by formula (I):

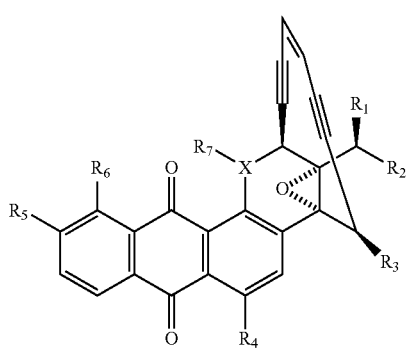

(I)

or a pharmaceutically acceptable salt thereof, wherein:

$R_1$, $R_2$, $R_3$, $R_4$, $R_5$, $R_6$ and $R_7$ are each independently: H, O, OH, F, Cl, Br, $CH_3$, R', OR', $NH_2$, NHR', $NR'_2$, SH, SR', C(O)R, $RCO_2R'$, halogen, alkyl, heteroatom substituted alkyl, unsaturated alkyl, polyunsaturated alkyl, aryl, heteroaryl, cycloalkyl, heteroatom-substituted analogs, alkenyl, alkyryl, acyl, alkoxy, heteroarylalkyl, heterocycloalkyl, cycloaliphatic, heterocycloaliphatic, arylalkyl, optionally substituted $C_1$-$C_{10}$ alkyl, optionally substituted aryl, optionally substituted alkaryl, optionally substituted alkoxyl, optionally substituted heteroaryl, optionally substituted arylalkoxyl, optionally substituted $C_2$-$C_{10}$ alkyl, optionally substituted acyl, NHC(=O)OR', NHC(=O)NHR', OC(=O)NHR', $(CH_2)_{1-4}$NHR', C(=O)R', or C(=O)OR', $N(R')_2$, NHC(=O)OR', OC(=O)NHR', OC(=O)R', SC(=O)R', or NHC(=O)R' or an amino acid side chain;

R' is H, halogen, O, $CH_3$, $C_1$-$C_{10}$ alkyl, $(CH_2)_n NH_2$, C(=O)$(CH_2)_n NH_2$, C(=O)CHR$^y$NH$_2$, or C(=O)R$^x$NH$_2$, $C_1$-$C_6$ alkyl, $(CH_2)_n NH_2$, optionally substituted $C_1$-$C_{10}$ alkyl, optionally substituted $C_1$-$C_{10}$ alkenyl, optionally substituted $C_1$-$C_{10}$ alkynyl, optionally substituted aryl, optionally substituted alkaryl, optionally substituted acyl; R$^y$ is an amino acid or amino acid side chain; R$^x$ is optionally substituted arylene, optionally substituted heteroarylene, optionally substituted alkylarylene, optionally substituted cycloalkylene, optionally substituted heterocycloalkylene, optionally substituted $C_1$-$C_6$ alkyl, optionally substituted cycloalkyl, optionally substituted heterocycloalkyl, optionally substituted arylalkyl, optionally substituted aryl, optionally substituted heteroaryl, and n is 2, 3, 4, 5, or 6; and, X is C, N, S, O or R'.

In one embodiment, the compound is

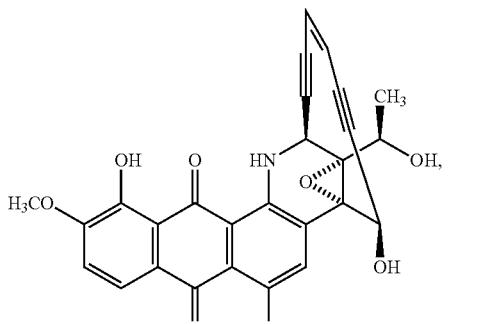

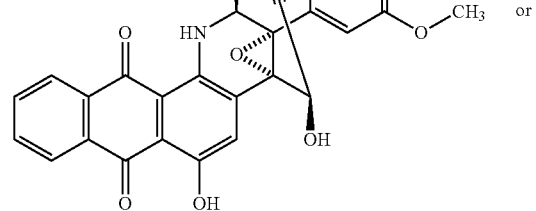

or

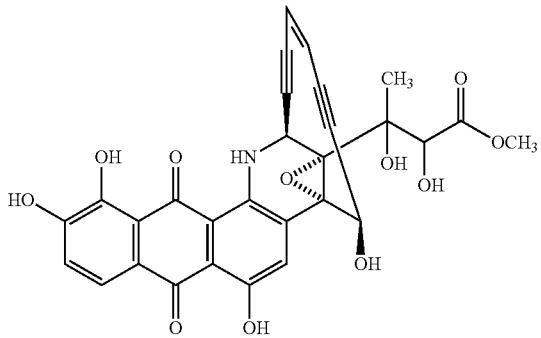

analogs, derivatives or pharmaceutically acceptable salts thereof.

In another embodiment, a compound comprises a structure represented by formula (I):

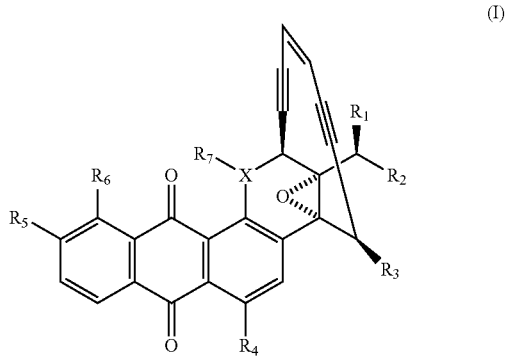

(I)

or a pharmaceutically acceptable salt thereof, wherein:
$R_1$, $R_2$, $R_3$, $R_4$, $R_5$, $R_6$ and $R_7$ are each independently: H, O, OH, F, Cl, Br, $CH_3$, R', OR', $NH_2$, NHR', $NR'_2$, SH, SR', C(O)R, $RCO_2R'$, halogen, alkyl, heteroatom substituted alkyl, unsaturated alkyl, polyunsaturated alkyl, aryl, heteroaryl, cycloalkyl, heteroatom-substituted analogs, alkenyl, alkyryl, acyl, alkoxy, heteroarylalkyl, heterocycloalkyl, cycloaliphatic, heterocycloaliphatic, arylalkyl, optionally substituted $C_1$-$C_{10}$ alkyl, optionally substituted aryl, optionally substituted alkaryl, optionally substituted alkoxyl, optionally substituted heteroaryl, optionally substituted arylalkoxyl, optionally substituted $C_2$-$C_{10}$ alkyl, optionally substituted acyl, NHC(=O)OR', NHC(=O)NHR', OC(=O)NHR', $(CH_2)_{1-4}$NHR', C(=O)R', or C(=O)OR', N(R')$_2$, NHC(=O)OR', OC(=O)NHR', OC(=O)R', SC(=O)R', or NHC(=O)R' or an amino acid side chain;

R' is H, halogen, O, $CH_3$, $C_1$-$C_{10}$ alkyl, $(CH_2)_n NH_2$, C(=O)$(CH_2)^n NH_2$, C(=O)CHR$^y$NH$_2$, or C(=O)R$^x$NH$_2$, $C_1$-$C_6$ alkyl, $(CH_2)_n NH_2$, optionally substituted $C_1$-$C_{10}$ alkyl, optionally substituted $C_1$-$C_{10}$ alkenyl, optionally substituted $C_1$-$C_{10}$ alkynyl, optionally substituted aryl, optionally substituted alkaryl, optionally substituted acyl; R$^y$ is an amino acid or amino acid side chain; R$^x$ is optionally substituted arylene, optionally substituted heteroarylene, optionally substituted alkylarylene, optionally substituted cycloalkylene, optionally substituted heterocycloalkylene, optionally substituted $C_1$-$C_6$ alkyl, optionally substituted cycloalkyl, optionally substituted heterocycloalkyl, optionally substituted arylalkyl, optionally substituted aryl, optionally substituted heteroaryl, and n is 2, 3, 4, 5, or 6; and, X is C, N, S, R'.

In another embodiment, a compound comprises a structure represented by formula (II):

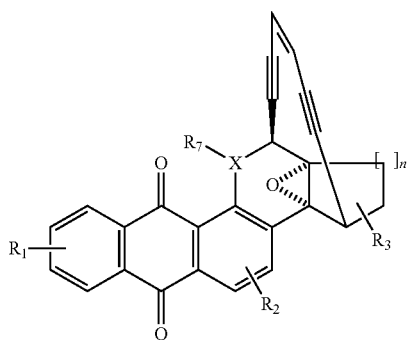

(II)

or a pharmaceutically acceptable salt thereof, wherein:
$R_1$, $R_2$, $R_3$, and $R_4$, are each independently: H, O, OH, F, Cl, Br, R', OR', $CH_3$, $NH_2$, NHR', NR'$_2$, SH, SR', C(O)R, RCO$_2$R', halogen, alkyl, heteroatom substituted alkyl, unsaturated alkyl, polyunsaturated alkyl, aryl, heteroaryl, cycloalkyl, heteroatom-substituted analogs, alkenyl, alkyryl, acyl, alkoxy, heteroarylalkyl, heterocycloalkyl, cycloaliphatic, heterocycloaliphatic, arylalkyl, optionally substituted $C_1$-$C_{10}$ alkyl, optionally substituted aryl, optionally substituted alkaryl, optionally substituted alkoxyl, optionally substituted heteroaryl, optionally substituted arylalkoxyl, optionally substituted $C_1$-$C_{10}$ alkyl, optionally substituted acyl, NHC(=O)OR', NHC(=O)NHR', OC(=O)NHR', $(CH_2)_{1-4}$NHR', C(=O)R', or C(=O)OR', N(R')$_2$, NHC(=O)OR', OC(=O)NHR', OC(=O)R', SC(=O)R', or NHC(=O)R' or an amino acid side chain, and n is 1, 2, 3, 4, 5, 6, 7, 8, 9, or 10;

R' is H, halogen, 0, $CH_3$, $C_1$-$C_{10}$ alkyl, $(CH_2)_n NH_2$, C(=O)$(CH_2)_n NH_2$, C(=O)CHR$^y$NH$_2$, or C(=O)R$^x$NH$_2$, $C_1$-$C_6$ alkyl, $(CH_2)_n NH_2$, optionally substituted $C_1$-$C_{10}$ alkyl, optionally substituted $C_1$-$C_{10}$ alkenyl, optionally substituted $C_1$-$C_{10}$ alkynyl, optionally substituted aryl, optionally substituted alkaryl, optionally substituted acyl; R$^y$ is an amino acid or amino acid side chain; R$^x$ is optionally substituted arylene, optionally substituted heteroarylene, optionally substituted alkylarylene, optionally substituted cycloalkylene, optionally substituted heterocycloalkylene, optionally substituted $C_1$-$C_{10}$ alkyl, optionally substituted cycloalkyl, optionally substituted heterocycloalkyl, optionally substituted arylalkyl, optionally substituted aryl, optionally substituted heteroaryl, and n is 2, 3, 4, 5, or 6; and, X is C, N, S or R'.

In another embodiment, a compound comprises a structure represented by formula (III):

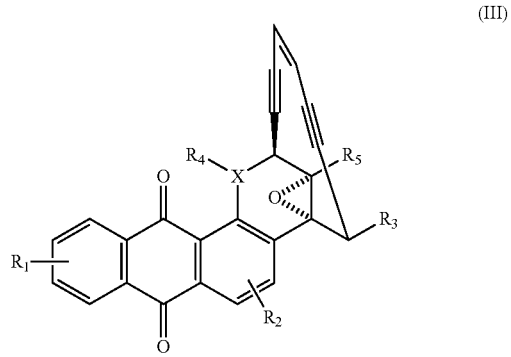

(III)

or a pharmaceutically acceptable salt thereof, wherein:
$R_1$, $R_2$, $R_3$, $R_4$ and $R_5$, are each independently: H, O, OH, F, Cl, Br, CR', R', OR', $NH_2$, NHR', NR'$_2$, SH, SR', C(O)R, RCO$_2$R', halogen, alkyl, heteroatom substituted alkyl, unsaturated alkyl, polyunsaturated alkyl, aryl, heteroaryl, cycloalkyl, heteroatom-substituted analogs, alkenyl, alkyryl, acyl, alkoxy, heteroarylalkyl, heterocycloalkyl, cycloaliphatic, heterocycloaliphatic, arylalkyl, optionally substituted $C_1$-$C_{10}$ alkyl, optionally substituted aryl, optionally substituted alkaryl, optionally substituted alkoxyl, optionally substituted heteroaryl, optionally substituted arylalkoxyl, optionally substituted $C_2$-$C_{10}$ alkyl, optionally substituted acyl, NHC(=O)OR', NHC(=O)NHR', OC(=O)NHR', $(CH_2)_{1-4}$NHR', C(=O)R', or C(=O)OR', N(R')$_2$, NHC(=O)OR', OC(=O)NHR', OC(=O)R', SC(=O)R', or NHC(=O)R' or an amino acid side chain;

R' and R are independently: H, O, $CH_3$, halogen, $C_1$-$C_{10}$ alkyl, $(CH_2)_n NH_2$, C(=O)$(CH_2)_n NH_2$, C(=O)CHR$^y$NH$_2$, or C(=O)R$^x$NH$_2$, $C_1$-$C_6$ alkyl, $(CH_2)_n NH_2$, optionally substituted $C_1$-$C_{10}$ alkyl, optionally substituted $C_1$-$C_{10}$ alkenyl, optionally substituted $C_1$-$C_{10}$ alkynyl, optionally substituted aryl, optionally substituted alkaryl, optionally substituted acyl; R$^y$ is an amino acid or amino acid side chain; R$^x$ is optionally substituted arylene, optionally substituted heteroarylene, optionally substituted alkylarylene, optionally substituted cycloalkylene, optionally substituted heterocycloalkylene, optionally substituted $C_1$-$C_6$ alkyl, optionally substituted cycloalkyl, optionally substituted heterocycloalkyl, optionally substituted arylalkyl, optionally substituted aryl, optionally substituted heteroaryl, and n is 1, 2, 3, 4, 5, or 6; and X is C, N, S or R'.

In another embodiment, a conjugate comprises a compound having a structure represented by formulae (I), (II) or (III) wherein the compound is conjugated to a targeting ligand.

In another embodiment, an antibody-drug conjugate comprises a compound having a structure represented by formulae (I), (II) or (III) wherein the compound is conjugated to an antibody and the antibody is specific for a tumor antigen or a target molecule or cell associated with a disease.

In another embodiment, the compound having a structure represented by formulae (I), (II) or (III) are encapsulated in a delivery vehicle, such, as for example, a liposome. In certain embodiments, delivery may occur by use of liposomes, nanocapsules, microparticles, microspheres, lipid particles, vesicles, optionally mixing with cell penetrating polypeptides, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out.

In one embodiment, the compound is

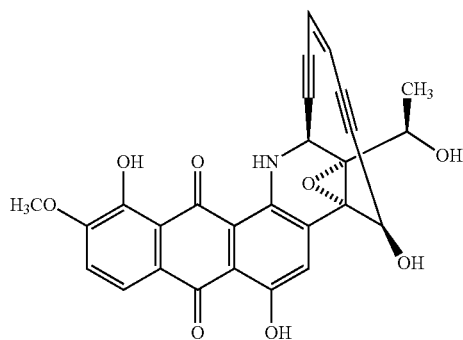

analogs, derivatives or pharmaceutically acceptable salts thereof.

In another embodiment the compound is

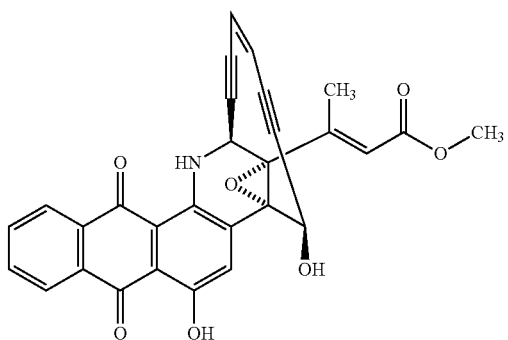

analogs, derivatives or pharmaceutically acceptable salts thereof.

In another embodiment the compound is

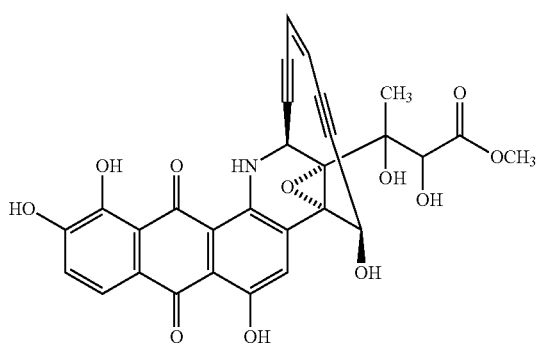

analogs, derivatives or pharmaceutically acceptable salts thereof.

In another embodiment, a pharmaceutical composition comprises a compound having a structure represented by formulae (I), (II) or (III).

In another embodiment, a compound having a structure represented by formulae (I), (II) or (III) wherein the compound comprises a detectable label.

Cells: The present invention also provides for cells comprising a nucleic acid or a vector as described above. In one embodiment, a cell comprises any of the vectors encoding for compound having a structure represented by formulae (I), (II) or (III).

In one embodiment, the vector expresses one or more compounds of:

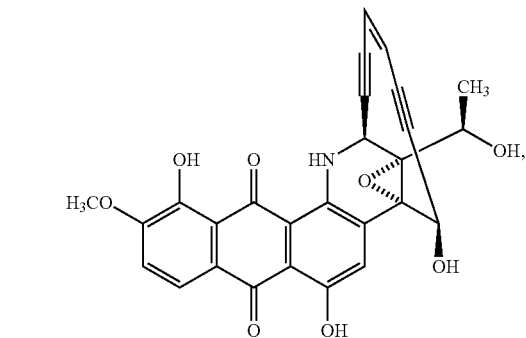

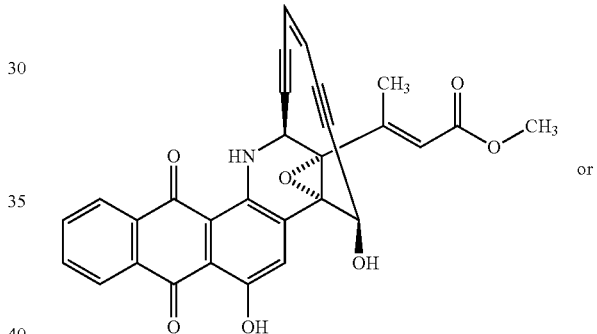

or

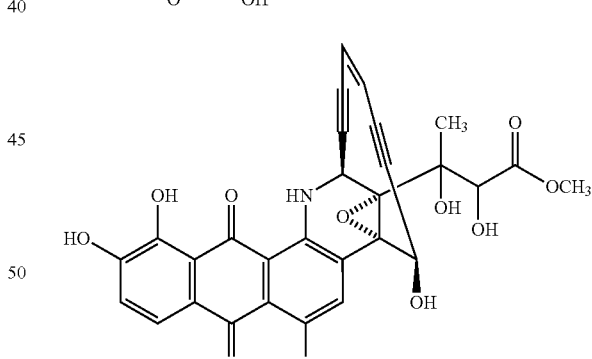

analogs, derivatives or pharmaceutically acceptable salts thereof.

Targeting Ligands: In some embodiments, the targeting ligands and the modified targeting ligands of the present invention may be of any kind presently known, or that become known, and includes peptides and non-peptides. The targeting ligands can be any compound that can bind a cell, either in a specific or non-specific manner. Generally, these can be antibodies (especially monoclonal antibodies and antibody fragments), adnectins (US Publication No.: 20070082365), interferons, lymphokines, hormones, growth factors, vitamins, integrins, carbohydrates, oligonucleotides, polynucleotides, peptides, polypeptides, modified peptides or oligonucleotides, modified polypeptides or polynucleotides, metals, organic or inorganic molecules, nutrient-transport molecules (such as transferrin), peptide nucleic acids, oligomers, or any other cell-binding molecule or substance.

In one embodiment, an antibody-drug conjugate comprising a compound according to any one of the structures represented by formulae (I), (II) and (III) are conjugated to an antibody, wherein the antibody is specific for a tumor antigen or a target molecule or cell associated with a disease.

In another embodiment, targeting ligand-drug conjugate comprises a structure represented by formula (IV) $(A)_xL$, wherein: L is a targeting ligand, x is 1, 2, 3, 4, 5, 6, 7, 8, 9, or 10; and A is selected from the group consisting of compounds having a general structure represented by formulae (I), (II) and (III).

In some embodiments, the antibody-drug conjugate further comprises one or more linking moieties comprising a structure represented by formula (V): $(A)_x(M)_yL_z$ wherein: M is a linking moiety; and, y and z are independently 0, 1, 2 or 3.

In some embodiments, the compound (A) is

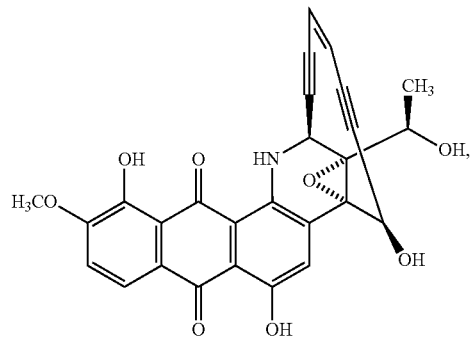

analogs, derivatives or pharmaceutically acceptable salts thereof.

In some embodiments, the compound (A) is

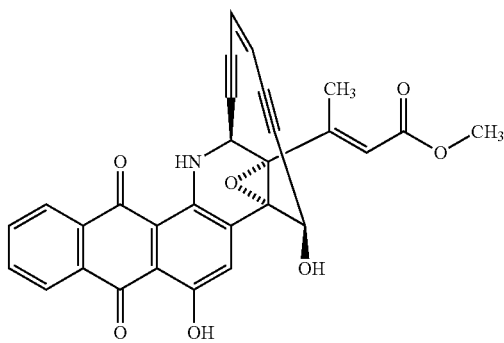

analogs, derivatives or pharmaceutically acceptable salts thereof.

In some embodiments, the compound (A) is

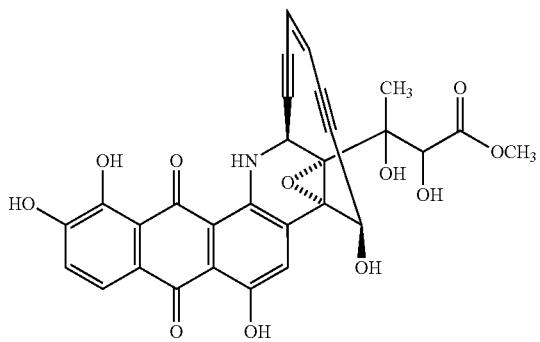

analogs, derivatives or pharmaceutically acceptable salts thereof.

It should be understood that the compound A represented in formulae (IV) or (V) can comprise one or more combinations of various compounds having structures represented by formulae (I), (II) or (III). Accordingly, the compound A can comprise two or more compounds which are identical.

Where the targeting ligand is an antibody (for example, a murine, human humanized, resurfaced or a chimeric or any other antibody known to one of skill in the art), it binds to an antigen that is a polypeptide and may be a transmembrane molecule (e.g. receptor) or a ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-13; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins, EpCAM, GD3, FLT3, PSMA, PSCA, MUC1, MUC16, STEAP, CEA, TENB2, EphA receptors, EphB receptors, folate receptor, mesothelin, cripto, $αv β_6$, integrins, VEGF, VEGFR, transferrin receptor, IRTA1, IRTA2, IRTA3, IRTA4, IRTA5; CD proteins such as CD2, CD3, CD4, CD5, CD6, CD8, CD11, CD14, CD19, CD20, CD21, CD22, CD23, CD25, CD26, CD28, CD30, CD33, CD36, CD37, CD38, CD40, CD44, CD52, CD55, CD56, CD59, CD70, CD79, CD80, CD81, CD103, CD105, CD134, CD137, CD138, CD152 or an antibody which binds to one or more tumor-associated antigens or cell-surface; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CD1a, CD1b, CD1c, CD18, an ICAM, VLA-4, EpCAM and VCAM; a tumor associated antigen such as HER2, HER3 or HER4 receptor; and fragments of any of the above-listed polypeptides.

Other antigens for antibodies encompassed by the present invention also include CD proteins, such as CD3, CD4, CD8, CD19, CD20, CD34, and CD46; members of the ErbB receptor family, such as the EGF receptor, HER2, HER3 or HER4 receptor; cell adhesion molecules, such as LFA-1, Mac1, p150.95, VLA-4, ICAM-1, VCAM, EpCAM, $\alpha_4\beta_7$ integrin, and $\alpha v\beta 3$ integrin including either alpha or beta subunits thereof (e.g. anti-CD1a, anti-CD18 or anti-CD1a antibodies); growth factors, such as VEGF; tissue factor (TF); TGF-$\beta$; alpha interferon (alpha-IFN); an interleukin, such as IL-8; IgE; blood group antigens Apo2, death receptor; flk2/flt3 receptor; obesity (OB) receptor; mpl receptor; CTLA-4; protein C etc. Other antibodies that can be used are antibodies to CD2, CD3, CD4, CD5, CD6, CD11, CD19, CD20, CD22, CD26, CD30, CD33, CD37, CD38, CD40, CD44, CD56, CD79, CD105, CD138, EphA receptors (e.g., EphA2 receptor), EphB receptors, EGFr, EGFRvIII, HER2, HER3, trastuzumab, pertuzumab mesothelin, cripto, $\alpha_v\beta_6$, integrins, VEGF, VEGFR, folate receptor (for example, FOLR1), transferrin receptor, GD3, EpCAM or an antibody which binds to one or more tumor-associated antigens or cell-surface receptors disclosed in US Publication No. 20080171040 or US Publication No. 20080305044.

Additional examples of targeting ligands that are conjugated to the compounds embodied herein include: aptamers, antibody mimetics, such as an affibody, a domain antibody (dAb), a nanobody, a unibody, a DARPin, an anticalin, a versabody, a duocalin, a lipocalin, an avimer, resurfaced antibodies (U.S. Pat. No. 5,639,641); humanized or fully human antibodies, selected from but not limited to, huMy9-6, huB4, huC242, huN901, DS6, CD38, IGF-IR, CNTO 95, B-B4, trastuzumab, pertuzumab, bivatuzumab, sibrotuzumab, and rituximab (see, e.g., U.S. Pat. Nos. 5,639,641, 5,665,357; and U.S. Pat. No. 7,342,110; Pedersen et al., (1994) *J. Mol. Biol.* 235, 959-973, Roguska et al., (1994) Proceedings of the National Academy of *Sciences, Vol* 91, 969-973; Colomer et al., *Cancer Invest.,* 19: 49-56 (2001), Heider et al., *Eur. J. Cancer,* 31A: 2385-2391 (1995), Welt et al., *J. Clin. Oncol.,* 12: 1193-1203 (1994), and Maloney et al., *Blood,* 90: 2188-2195 (1997)); and epitope-binding fragments of antibodies such as sFv, Fab, Fab', and F(ab')$_2$ (Parham, *J. Immunol.* 131:2895-2902 (1983); Spring et al, *J. Immunol.* 113:470-478 (1974); Nisonoff et al, *Arch. Biochem. Biophys.* 89:230-244 (1960)). Additional targeting ligands include other cell-binding proteins and polypeptides exemplified by, but not limited to: ankyrin repeat proteins (DARPins; Zahnd et al., *J. Biol. Chem.,* 281, 46, 35167-35175, (2006); Binz, H. K., Amstutz, P. & Pluckthun, A. (2005) *Nature Biotechnology,* 23, 1257-1268) or ankyrin-like repeats proteins or synthetic peptides described, for example, in U.S. patent Publication Number 20070238667; U.S. Pat. No. 7,101,675); interferons (e.g. $\alpha$, $\beta$, $\gamma$); lymphokines such as IL-2, IL-3, IL-4, IL-6; hormones such as insulin, TRH (thyrotropin releasing hormones), MSH (melanocyte-stimulating hormone), steroid hormones, such as androgens and estrogens; vitamins such as folic acid; growth factors and colony-stimulating factors such as EGF, TGF-$\alpha$, G-CSF, M-CSF and GM-CSF (Burgess, *Immunology Today* 5:155-158 (1984)); and transferrin (O'Keefe et al, *J. Biol. Chem.* 260:932-937 (1985)).

Monoclonal antibody techniques allow for the production of specific targeting ligands in the form of monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of sFv (single chain variable region), specifically human sFv (see, e.g., Griffiths et al, U.S. Pat. No. 5,885,793).

Selection of the appropriate targeting ligand is a matter of choice that depends upon the particular cell population that is to be targeted, but in general monoclonal antibodies and epitope binding fragments thereof are preferred, if an appropriate one is available.

For example, the monoclonal antibody My9 is a murine IgG$_{2a}$ antibody that is specific for the CD33 antigen found on Acute Myeloid Leukemia (AML) cells (Roy et al. *Blood* 77:2404-2412 (1991)) and can be used to treat AML patients. Similarly, the monoclonal antibody anti-B4 is a murine IgG$_1$, which binds to the CD19 antigen on B cells (Nadler et al. *J. Immunol.* 131:244-250 (1983)) and can be used if the target cells are B cells or diseased cells that express this antigen such as in non-Hodgkin's lymphoma or chronic lymphoblastic leukemia. Similarly, the antibody N901 is a murine monoclonal IgG$_1$ antibody that binds to CD56 found on small cell lung carcinoma cells and on cells of other tumors of the neuroendocrine origin (Roy et al. *J. Nat. Cancer Inst.* 88:1136-1145 (1996)), C242 antibody that binds to the CanAg antigen, pertuzumab, trastuzumab that binds to HER2/neu, and anti-EGF receptor antibody.

Additionally, GM-CSF, which binds to myeloid cells, can be used as a targeting ligand to diseased cells from acute myelogenous leukemia. IL-2, which binds to activated T-cells, can be used for prevention of transplant graft rejection, for therapy and prevention of graft-versus-host disease, and for treatment of acute T-cell leukemia. MSH, which binds to melanocytes, can be used for the treatment of melanoma. Folic acid, which targets the folate receptor expressed on ovarian and other cancers, is also a suitable targeting ligand.

Cancers of the breast and testes can be successfully targeted with estrogen (or estrogen analogues) or androgen (or androgen analogues), respectively, as targeting ligands.

In an embodiment, the antibody-drug conjugates of the present invention include an antibody, (e.g., a monoclonal antibody, an antibody fragment, or an antibody derivative) that is selected based on its specificity for an antigen expressed on a target cell, or at a target site, of interest. A wide variety of tumor-specific or other disease-specific antigens have been identified and antibodies to those antigens have been used or proposed for use in the treatment of such tumors or other diseases. Poon et al., in the *Journal of*

*Biological Chemistry*, 270:8571-8577 (1995), report the production of chimeric IgM antibodies.

The antibodies that are known in the art can be used in the conjugates of the invention, in particular for the treatment of the disease with which the target antigen is associated. Non-limiting examples of target molecules or antigens (and examples of their associated diseases) to which an antibody-partner molecule conjugate of the invention can be targeted include: Her2 (breast cancer), CD20 (lymphomas), EGFR (solid tumors), CD22 (lymphomas, including non-Hodgkin's lymphoma), CD52 (chronic lymphocytic leukemia), CD33 (acute myelogenous leukemia), CD4 (lymphomas, autoimmune diseases, including rheumatoid arthritis), CD30 (lymphomas, including non-Hodgkin's lymphoma), Muc18 (melanoma), integrins (solid tumors), PSMA (prostate cancer, benign prostatic hyperplasia), CEA (colorectal cancer), CD1a (psoriasis), CD70 (autoimmune diseases and cancer, including renal cell carcinoma), CD80 (psoriasis), CD23 (asthma), CD40L (immune thromobcytopenic CTLA4 (T cell lymphomas) and BLys (autoimmune diseases, including systemic lupus erythematosus). Additional non-limiting examples of target antigens to which an antibody-partner molecule conjugate of the invention can be targeted include: CD19, Glypican-3, RG-1, MUC1, MUC16, TMPRSS4, Fibronectin ED-B, IRTA2, IRTA3, IRTA4, IRTA5, and Ephrin receptors.

Further included are monoclonal antibodies including Trastuzumab (HERCEPTIN™), described in Beeram et al., *J. Clin. Oncol.* 26, 1028 (2008, May 20 Supp.), alemtuzumab, abciximab, biciromab (REOPRO™), omalizumab, BR96, eculizumab, MH-1, ATM-027, SC-1, bivatuzumab, BMS-188667, BMS-224818, SGN-15, CAT-213, J-695, rituximab (RITUXAN™), CEA-Scan, sulesomab, palivizumab (SYNAGIS™), basiliximab (SIMULECT™), daclizumab (ZENAPAX™), ONCOLYM™, CARORX™, apolizumab, fontolizumab, NUVION™, SMART anti-L-selectin Mab, TMA-15, YM-337, M60.1, WX-G250, VITAXIN™, mepolizumab, pascolizumab, tositumomab, efalizumab, $^{99m}$Tc-fanolesomab, metelimumab, CAL, MRA, MLN-2704, OncoRad PR356, licilimomab, MAb-81C6, clenoliximab, MELIMMUNE™, HumaRAD16.88™, KW-2871, MLN-02, MDX-210, MDX-37, MDX-H210, 3F8, EMD-72000, SS (dsFv) PE38, infliximab (REMICADE™), $^{111}$Incapromab pendetide; trastuzumab (HERCEPTIN™), TNX-901, 5-D12, THERACIM-h-R3™, TriAb, TRX-4, TRIGEM™, HRS-3/A9, BTI-322, siplizumab, MYCOGRAB™, 1NG-1(heMAb), HepeX-B, pexelizumab, orgovomab, natalizumab, bevacizumab, cetuximab, epratuzumab, afelimomab, MDX-RA, inolimomab, lintuzumab, CEAVAC™, mPA7, and mhoe-4.

In addition, one of skill in the art does not need to rely on previously identified antibodies to practice the instant invention, but instead can prepare an antibody to a target of interest for use in the present invention using standard antibody production techniques. Several of such techniques have been described and others are well known in the art, for example those described in Lonberg, N. et al. (1994) *Nature* 368(6474): 856 859; Fishwild, D. et al. (1996) *Nature Biotechnology* 14: 845-851.

In another embodiment, the antibodies of the instant invention are Affibodies. Affibody molecules represent a new class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K, et al. *Nat Biotechnol* 1997; 15:772-7. Ronmark J, et al. *Eur J Biochem* 2002; 269:2647-55.). The simple, robust structure of Affibody molecules in combination with their low molecular weight (6 kDa), make them suitable for a wide variety of applications, for instance, as detection reagents (Ronmark J, et al. *J Immunol Methods* 2002; 261:199-211) and to inhibit receptor interactions (Sandstorm K, et al. *Protein Eng* 2003; 16:691-7). Further details of Affibodies and methods of production thereof may be obtained by reference to U.S. Pat. No. 5,831,012.

In an embodiment, the antibodies of the instant application are Domain Antibodies (dAbs). dAbs are the smallest functional binding units of antibodies, corresponding to the variable regions of either the heavy (VH) or light (VL) chains of human antibodies. Domain Antibodies have a molecular weight of approximately 13 kDa. Domantis has developed a series of large and highly functional libraries of fully human VH and VL dAbs (more than ten billion different sequences in each library), and uses these libraries to select dAbs that are specific to therapeutic targets. In contrast to many conventional antibodies, Domain Antibodies are well expressed in bacterial, yeast, and mammalian cell systems. Further details of domain antibodies and methods of production thereof may be obtained by reference to U.S. Pat. Nos. 6,291,158; 6,582,915; 6,593,081; 6,172,197; 6,696,245.

In another embodiment the antibodies of the instant invention are Nanobodies. Nanobodies are antibody-derived therapeutic proteins that contain the unique structural and functional properties of naturally-occurring heavy-chain antibodies. These heavy-chain antibodies contain a single variable domain ($VH_H$) and two constant domains (CH2 and CH3). Importantly, the cloned and isolated $VH_H$ domain is a perfectly stable polypeptide harboring the full antigen-binding capacity of the original heavy-chain antibody. Nanobodies have a high homology with the VH domains of human antibodies and can be further humanized without any loss of activity. Importantly, nanobodies have a low immunogenic potential, which has been confirmed in primate studies with nanobody lead compounds.

Nanobodies combine the advantages of conventional antibodies with important features of small molecule drugs. Like conventional antibodies, Nanobodies show high target specificity, high affinity for their target and low inherent toxicity. However, like small molecule drugs they can inhibit enzymes and readily access receptor clefts. Furthermore, Nanobodies are extremely stable, can be administered by means other than injection and are easy to manufacture. Other advantages of Nanobodies include recognizing uncommon or hidden epitopes as a result of their small size, binding into cavities or active sites of protein targets with high affinity and selectivity due to their unique 3-dimensional, drug format flexibility, tailoring of half-life and ease and speed of drug discovery.

Nanobodies are encoded by single genes and are efficiently produced in almost all prokaryotic and eukaryotic hosts e.g. *E. coli* (see e.g. U.S. Pat. No. 6,765,087), moulds (for example, *Aspergillus* or *Trichoderma*) and yeast (for example, *Saccharomyces, Kluyveromyces, Hansenula* or *Pichia*) (see e.g. U.S. Pat. No. 6,838,254). The production process is scalable and multi-kilogram quantities of Nanobodies have been produced. Because Nanobodies exhibit a superior stability compared with conventional antibodies, they can be formulated as a long shelf-life, ready-to-use solution.

In another embodiment the antibodies of the instant invention are UniBodies. UniBodies are a stable, smaller antibody format with an anticipated longer therapeutic window than current small antibody formats. IgG4 antibodies are considered inert and thus do not interact with the immune system. The UniBody is about half the size of a regular $IgG_4$ antibody. This small size can be a great benefit when treating some forms of cancer, allowing for better distribution of the molecule over larger solid tumors and potentially increasing efficacy.

Fabs typically do not have a very long half-life. UniBodies, however, were cleared at a similar rate to whole $IgG_4$ antibodies and were able to bind as well as whole antibodies and antibody fragments in pre-clinical studies. Other antibodies primarily work by killing the targeted cells whereas UniBodies only inhibit or silence the cells.

In another embodiment, the target binding agent is an aptamer.

In another embodiment, the target binding agents are specific for different cell types or different cell-specific molecules or differing specificities on the same cell-specific molecule or combinations thereof. The number of targeting binding agents and specificities of each molecule is limited only by the imagination of the user.

Conjugation:

Any one of several different reactive groups of a targeting ligand can be a conjugation site, including: amino groups in lysine residues, pendant carbohydrate moieties, carboxylic acid groups, disulfide groups, and thiol groups. For reviews on antibody reactive groups suitable for conjugation, see, e.g., Garnett, *Adv. Drug Delivery Rev.* 53 (2001), 171-216 and Dubowchik and Walker, Pharmacology & Therapeutics 83 (1999), 67-123.

In an embodiment, a targeting ligand is conjugated via a lysine ε-amino group. Most antibodies have multiple exposed lysine ε-amino groups, which can be conjugated via amide, urea, thiourea, or carbamate bonds using techniques known in the art, including modification with a heterobifunctional agent.

In another embodiment, a targeting ligand is conjugated via a carbohydrate side chain, as many antibodies are glycosylated. The carbohydrate side chain can be oxidized with periodate to generate aldehyde groups, which in turn can be reacted with amines to form an imine group, such as in a semicarbazone, oxime, or hydrazone. If desired, the imine group can be converted to a more stable amine group by reduction with sodium cyanoborohydride.

In yet another embodiment, a targeting ligand is conjugated via a carboxylic acid group. In one embodiment, a terminal carboxylic acid group is functionalized to generate a carbohydrazide, which is then reacted with an aldehyde-bearing conjugation moiety. See Fisch et al., *Bioconjugate Chemistry* 1992, 3, 147-153.

In yet another embodiment, a targeting ligand is conjugated via a disulfide group bridging a cysteine residue on antibody Z and a sulfur on the other portion of the conjugate. Some antibodies lack free thiol (sulfhydryl) groups but have disulfide groups, for example in the hinge region. In such case, free thiol groups can be generated by reduction of native disulfide groups. The thiol groups so generated can then be used for conjugation. See, e.g., Packard et al., *Biochemistry* 1986, 25, 3548-3552; King et al., *Cancer Res.* 54, 6176-6185 (1994); and Doronina et al., *Nature Biotechnol.* 21(7), 778-784 (2003).

In yet another embodiment, lysine ε-amino groups can be modified with heterobifunctional reagents such as 2-iminothiolane or N-succinimidyl-3-(2-pyridyldithio)-propionate (SPDP), converting an ε-amino group into a thiol or disulfide group—creating a cysteine surrogate.

In yet another preferred embodiment, a targeting ligand is conjugated via the nucleophilic addition product of a thiol group to an acceptor moiety. A preferred acceptor moiety is a maleimide group.

The conjugation of a targeting molecule will, of course, depend on the type of targeting agent, for example, sequences encoding a targeting ligand can be included into the genome encoding the compound.

In other embodiments, the targeting ligand provides for the intracellular uptake of the compound and may, optionally comprise one or more groups or linker molecules which are cleaved intracellularly thereby releasing the compound. The groups can be cleavable under physiological conditions, preferably selected such that it is relatively stable while the conjugate is in general circulation in the blood plasma, but is readily cleaved once the conjugate reaches its site of intended action, that is, near, at, or within the target cell. Preferably, the conjugate is internalized by endocytosis by a target cell upon binding of the targeting ligand to an antigen or other target molecule displayed on the surface of the target cell. Subsequently, cleavage of the groups or linker molecules occurs in a vesicular body of the target cell (an early endosome, a late endosome, or, especially, a lysosome). For example, the target ligand-compound conjugate comprises a pH sensitive group or a disulfide bond. The pH in blood plasma is slightly above neutral, while the pH inside a lysosome is acidic, circa 5. Thus, a group whose cleavage is acid catalyzed will cleave at a rate several orders of magnitude faster inside a lysosome than in the blood plasma rate. Examples of suitable acid-sensitive groups include cis-aconityl amides and hydrazones, as described in Shen et al., U.S. Pat. No. 4,631,190 (1986); Shen et al., U.S. Pat. No. 5,144,011 (1992); Shen et al., *Biochem. Biophys. Res. Commun.* 102, 1048-1054 (1981) and Yang et al., *Proc. Natl. Acad. Sci.* (USA), 85, 1189-1193 (1988).

In the case of disulfide cleavable groups, disulfides can be cleaved by a thiol-disulfide exchange mechanism, at a rate dependent on the ambient thiol concentration. As the intracellular concentration of glutathione and other thiols is higher than their serum concentrations, the cleavage rate of a disulfide will be higher intracellularly. Further, the rate of thiol-disulfide exchange can be modulated by adjustment of the steric and electronic characteristics of the disulfide (e.g., an alkyl-aryl disulfide versus an alkyl-alkyl disulfide; substitution on the aryl ring, etc.), enabling the design of disulfide linkages that have enhanced serum stability or a particular cleavage rate (see, e.g., Thorpe et al., *Cancer Res.* 48, 6396-6403 (1988); Santi et al., U.S. Pat. No. 7,541,530 B2 (2009); Ng et al., U.S. Pat. No. 6,989,452 B2 (2006); Boyd et al., U.S. Pat. No. 7,691,962 B2; and Sufi et al., US 2010/0145036 A1.

Enediynes as Ideal Payload Candidates for Anticancer ADCs.

ADCs provide the possibility of selectively ablating cancer cells by combining the specificity of a monoclonal antibody (mAB) for a target antigen with the delivery of a highly potent cytotoxic agent. The ideal number of drug molecules per mAB for most current ADCs appears to be about four. Underconjugation can decrease potency of the resultant ADCs, whereas overconjugation can lead to decreased circulation half-life, reduced tolerability, and impaired antigen binding.

In embodiments, the preferred enediyne compounds are highly cytotoxic and active in many tumor types having a range of at least about 0.1 nM to about 100 pM. In some embodiments the payload molecules have a range of about 1 nM to 10 pM. The enediynes represent some of the most cytotoxic molecules in existence today (for example, the $IC_{50s}$ of CAL and C-1027 towards selected cancer cell lines are in the range of 10 pM to $10^{-3}$ pM). While the enediynes are most known for their activity by DNA DSBs, the inventors have discovered ICL as an alternative mode of action for the enediyne family of anticancer agents and engineered C-1027 analogues capable of DNA DSBs, ICLs, or both. The inventors have further demonstrated that the ICL property of the enediynes can be exploited to target solid tumors or other cancer cells under hypoxic environments, which do not respond well to enediynes that predominantly induce oxygen dependent DSBs. The exquisite potency and mechanisms of action of the enediynes make them ideal payload candidates for ADCs. However, enediynes are extremely scarce, and only 11 enediynes are known to date, most of which are produced in trace quantities, intrinsically unstable, produced by rare Actinomycetes that are refractory to all means of genetic manipulations for either titer improvement or analogue generation, or simply not available in sufficient quantities for a full evaluation as ADC payload candidates.

Therefore, in certain aspects, the invention provides for new enediynes, with varying mechanisms and potency, functional groups for linkage, solubility to enable the reaction with antibodies, prolonged stability in formulation, which can be reliably produced in sufficient quantities by microbial fermentation of genetically amenable *Streptomyces* species. In embodiments, the invention provides for producing enediyne compounds which are potent, stable, permeable, tractable and each compound's efflux.

Therapeutic Uses

In an embodiment, a method of treating a subject diagnosed with cancer, comprises administering to the subject a therapeutically effective amount of a compound having a structural formula of (I), (II) or (II). In some embodiments, the compound is conjugated to a targeting ligand. In some embodiments, the targeting ligand specifically binds to a tumor antigen. In other embodiments, the targeting ligand specifically binds to antigens or markers associated with a disease or infectious organism, such as, for example, a virus.

Compounds of this invention or their conjugates can be used for treating diseases such as, but not limited to, hyperproliferative diseases, including: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; ovarian cancer; small cell and non-small cell lung cancer (SCLC and NSCLC); breast cancer sarcomas, such as fibrosarcoma, malignant fibrous histiocytoma, embryonal rhabdomyosarcoma, leiomysosarcoma, neurofibrosarcoma, osteosarcoma, synovial sarcoma, liposarcoma, and alveolar soft part sarcoma; leukemias such as acute promyelocytic leukemia (APL), acute myelogenous leukemia (AML), acute lymphoblastic leukemia (ALL), and chronic myelogenous leukemia (CML); neoplasms of the central nervous systems, particularly brain cancer; multiple myeloma (MM), lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. Clinically, practice of the methods and use of compositions described herein will result in a reduction in the size or number of the cancerous growth and/or a reduction in associated symptoms (where applicable). Pathologically, practice of the method and use of compositions described herein will produce a pathologically relevant response, such as: inhibition of cancer cell proliferation, reduction in the size of the cancer or tumor, prevention of further metastasis, and inhibition of tumor angiogenesis. The method of treating such diseases comprises administering a therapeutically effective amount of an inventive combination to a subject. The method may be repeated as necessary. Especially, the cancer can be colorectal cancer, liver cancer, prostate cancer, breast cancer, melanoma, glioblastoma, lung cancer, pancreatic cancer, ovarian cancer, multiple myeloma, renal cancer, leukemia (especially ALL, APL, or AML), or lymphoma.

The compounds or conjugates thereof may also have utility in the treatment of other diseases or conditions.

In embodiments, one or more compounds of Formula (I), (II) (III) and conjugates thereof are administered in therapeutically effective doses to patients in need of therapy. Patients in need of therapy comprise those at risk of developing a certain condition, disease or disorder (e.g. due to genetic, environmental or physical attributes, such as for example, obesity). Patients in need of therapy also include those afflicted with a condition, disease or disorder. The diseases or disorders comprise, for example: autoimmune diseases, cancer, inflammatory diseases, neurological diseases or disorders, neuroinflammatory diseases or disorders, cardiovascular disease, obesity, diseases or disorders caused by infectious agents such as, for example, viruses, bacteria, fungi, prions, or parasites. For example, the compounds of Formula I may be ligands for: an autoimmune molecule, an immune cell associated with autoimmunity or inflammation (e.g. lymphocytes), a foreign antigen, cytokines etc.

Examples of autoimmune diseases or disorders embodied herein, include without limitation: acute disseminated encephalomyelitis (ADEM), acute necrotizing hemorrhagic leukoencephalitis, Addison's disease, agammaglobulinemia, allergic asthma, allergic rhinitis, alopecia areata, amyloidosis, ankylosing spondylitis, anti-GBM/anti-TBM nephritis, antiphospholipid syndrome (APS), autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune pancreatitis, autoimmune retinopathy, autoimmune thrombocytopenic purpura (ATP), autoimmune thyroid disease, axonal & neuronal neuropathies, Balo disease, Behcet's disease, bullous pemphigoid, cardiomyopathy, Castlemen disease, celiac sprue (non-tropical), Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogan's syndrome, cold agglutinin disease, congenital heart block, coxsackie myocarditis, CREST disease, essential mixed cryoglobulinemia, demyelinating neuropathies, dermatomyositis, Devic's disease (neuromyelitis optica), discoid lupus, Dressler's syndrome, endometriosis, eosinophillic fasciitis, erythema nodosum, experimental allergic encephalomyelitis, Evan's syndrome, fibromyalgia, fibrosing alveolitis, giant cell arteritis (temporal arteritis), glomerulonephritis, Goodpasture's syndrome, Grave's disease, Guillain-Barre syndrome, Hashimoto's encephalitis, Hashimoto's thyroiditis, hemolytic anemia, Henock-Schoniein purpura, herpes gestationis, hypogammaglobulinemia, idiopathic thrombocytopenic purpura (ITP), IgA nephropathy, immunoregulatory lipoproteins, inclusion body myositis, insulin-dependent diabetes (type 1), interstitial cystitis, juvenile arthritis, juvenile diabetes, Kawasaki syndrome, Lambert-Eaton syndrome, leukocytoclastic vasculitis, lichen planus, lichen sclerosus, ligneous conjunctivitis, linear IgA disease (LAD), Lupus (SLE), Lyme disease, Meniere's disease, microscopic polyangitis, mixed connective tissue disease (MCTD), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, Parsonnage-Turner syndrome, pars plantis (peripheral uveitis), pemphigus, *Pemphigus vulgaris*, peripheral neuropathy, perivenous encephalomyelitis, pernicious anemia, POEMS syndrome, polyarteritis nodosa, type I, II & III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasis, Raynaud's phenomena, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Slogren's syndrome, sperm and testicular autoimmunity, stiff person syndrome, subacute bacterial endocarditis (SBE), sympathetic ophthalmia, Takayasu's arteritis, temporal arteritis/giant cell arteries, thrombocytopenic purpura (TPP), Tolosa-Hunt syndrome, transverse myelitis, ulcerative colitis, undifferentiated connective tissue disease (UCTD), uveitis, vasculitis, vesiculobullous dermatosis, vitiligo or Wegener's granulomatosis or, chronic active hepatitis, primary biliary cirrhosis, cadilated cardiomyopathy, myocarditis, autoimmune polyendocrine syndrome type I (APS-I), cystic fibrosis vasculitides, acquired hypoparathyroidism, coronary artery disease, pemphigus foliaceus, pemphigus vulgaris, Rasmussen encephalitis, autoimmune gastritis, insulin hypoglycemic syndrome (Hirata disease), Type B insulin resistance, acanthosis, systemic lupus erythematosus (SLE), pernicious anemia, treatment-resistant Lyme arthritis, polyneuropathy, demyelinating diseases, atopic dermatitis, autoimmune hypothyroidism, vitiligo, thyroid associated ophthalmopathy, autoimmune coeliac disease, ACTH deficiency, dermatomyositis, Sjogren syndrome, systemic sclerosis, progressive systemic sclerosis, morphea, primary antiphospholipid syndrome, chronic idiopathic urticaria, connective tissue syndromes, necrotizing and crescentic glomerulonephritis (NCGN), systemic vasculitis, Raynaud syndrome, chronic liver disease, visceral leishmaniasis, autoimmune Cl deficiency, membrane proliferative glomerulonephritis (MPGN), prolonged coagulation time, immunodeficiency, atherosclerosis, neuronopathy, paraneoplastic pemphigus, paraneoplastic stiff man syndrome, paraneoplastic encephalomyelitis, subacute autonomic neuropathy, cancer-associated retinopathy, paraneoplastic opsoclonus myoclonus ataxia, lower motor neuron syndrome and Lambert-Eaton myasthenic syndrome.

Examples of infectious diseases, include, but are not limited to, Acquired immunodeficiency syndrome (AIDS), Anthrax, Botulism, Brucellosis, Chancroid, Chlamydial infection, Cholera, Coccidioidomycosis, Cryptosporidiosis, Cyclosporiasis, Diphtheria, Ehrlichiosis, Arboviral Encephalitis, Enterohemorrhagic *Escherichia coli* (*E. coli*), Giardiasis, Gonorrhea, *Haemophilus influenzae*, Hansen's disease (leprosy), Hantavirus pulmonary syndrome, Hemolytic uremic syndrome, Hepatitis A, Hepatitis B, Hepatitis C, Human immunodeficiency virus (HIV), Legionellosis, Listeriosis, Lyme disease, Malaria, Measles, Meningococcal disease, Mumps, Pertussis (whooping cough), Plague, Paralytic Poliomyelitis (polio), Psittacosis (parrot fever), Q Fever, Rabies, Rocky Mountain spotted fever, Rubella, Congenital rubella syndrome, *Salmonellosis*, Severe acute respiratory syndrome (SARS), Shigellosis, Smallpox, Streptococcal disease (invasive Group A), Streptococcal toxic shock syndrome (STSS), *Streptococcus pneumoniae*, Syphilis, Tetanus, Toxic shock syndrome, Trichinosis, Tuberculosis, Tularemia, Typhoid fever, Vancomycin-Intermediate/Resistant *Staphylococcus aureus*, Varicella, Yellow fever, variant Creutzfeldt-Jakob disease (vCJD), Dengue fever, Ebola hemorrhagic fever, Echinococcosis (Alveolar Hydatid disease), Hendra virus infection, Human monkeypox, Influenza A H5N1 (avian influenza), Lassa fever, Marburg hemorrhagic fever, Nipah virus, O'nyong-nyong fever, Rift Valley fever, Venezuelan equine encephalitis, and West Nile virus.

Other examples are neurodegenerative diseases, stroke, hypovolemic shock, traumatic shock, reperfusion injury, multiple sclerosis, AIDS-associated dementia, neuron toxicity, Alzheimer's disease, head trauma, adult respiratory disease (ARDS), acute spinal cord injury, Huntington's disease, Parkinson's disease and Charcot-Marie-Tooth (CMT) disease.

Accordingly, the targeting ligand can be directed to any one or more antigens associated with such diseases or disorders.

The compounds of this invention can also be used in combination with other chemotherapeutic or therapeutic agents. The compounds of this invention or their conjugates can be administered in combination with, pre-, post-administration of the compounds or their conjugates. The therapeutic agents, include, without limitation, antibodies, alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, immunomodulators, microtubule stabilizers, nucleoside (purine or pyrimidine) analogs, nuclear export inhibitors, proteasome inhibitors, topoisomerase (I or II) inhibitors, tyrosine kinase inhibitors, and serine/threonine kinase inhibitors. Specific therapeutic agents include adalimumab, ansamitocin P3, auristatin, bendamustine, bevacizumab, bicalutamide, bleomycin, bortezomib, busulfan, callistatin A, camptothecin, capecitabine, carboplatin, carmustine, cetuximab, cisplatin, cladribin, cytarabin, cryptophycins, dacarbazine, dasatinib, daunorubicin, docetaxel, doxorubicin, duocarmycin, dynemycin A, epothilones, etoposide, floxuridine, fludarabine, 5-fluorouracil, gefitinib, gemcitabine, ipilimumab, hydroxyurea, imatinib, infliximab, interferons, interleukins, β-lapachone, lenalidomide, irinotecan, maytansine, mechlorethamine, melphalan, 6-mercaptopurine, methotrexate, mitomycin C, nilotinib, oxaliplatin, paclitaxel, procarbazine, suberoylanilide hydroxamic acid (SAHA), 6-thioguanidine, thiotepa, teniposide, topotecan, trastuzumab, trichostatin A, vinblastine, vincristine, and vindesine.

The compounds of the present invention can be administered in vitro, in vivo and/or ex vivo to treat patients and/or to modulate the growth of selected cell populations including, for example, cancer of the lung, blood, plasma, breast, colon, prostate, kidney, pancreas, brain, bones, ovary, testes, and lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, and AIDS; and parasite infections, such as giardiasis, amoebiasis, schistosomiasis, and the like. Preferably, the compounds and chemotherapeutic agents of the invention are administered in vitro, in vivo and/or ex vivo to treat cancer in a patient and/or to modulate the growth of cancer cells, including, for example, cancer of the blood, plasma, lung, breast, colon, prostate, kidney, pancreas, brain, bones, ovary, testes, and lymphatic organs; more preferably lung, colon prostrate, plasma, blood or colon cancer.

"Modulating the growth of selected cell populations" includes inhibiting the proliferation of selected cell populations (e.g., multiple myeloma cell populations, such as MOLP-8 cells, OPM2 cells, H929 cells, and the like) from dividing to produce more cells; reducing the rate of increase in cell division as compared, for example, to untreated cells; killing selected cell populations; and/or preventing selected cell populations (such as cancer cells) from metastasizing. The growth of selected cell populations can be modulated in vitro, in vivo or ex vivo.

In the methods of the present invention, the targeting ligand drug conjugates can be administered in vitro, in vivo, or ex vivo. The targeting ligand drug conjugates can be used with suitable pharmaceutically acceptable carriers, diluents, and/or excipients, which are well known, and can be determined, by one of skill in the art as the clinical situation warrants. Examples of suitable carriers, diluents and/or excipients include: (1) Dulbecco's phosphate buffered saline, pH about 6.5, which would contain about 1 mg/ml to 25 mg/ml human serum albumin, (2) 0.9% saline (0.9% w/v NaCl), and (3) 5% (w/v) dextrose.

The compounds and compositions described herein may be administered in appropriate form, e.g. parenterally, intravenously. For parenteral administration, the compounds or compositions can be aqueous or nonaqueous sterile solutions, suspensions or emulsions. Propylene glycol, vegetable oils and injectable organic esters, such as ethyl oleate, can be used as the solvent or vehicle. The compositions can also contain adjuvants, emulsifiers or dispersants.

The compositions can also be in the form of sterile solid compositions that can be dissolved or dispersed in sterile water or any other injectable sterile medium.

The "therapeutically effective amount" can also be determined by reference to standard medical texts, such as the Physicians' Desk Reference, 69$^{th}$ Edition, 2015. The patient is preferably an animal, more preferably a mammal, most preferably a human. The patient can be male or female, and can be an infant, child or adult.

Examples of suitable protocols of targeting ligand drug conjugates (administration are as follows. The conjugates can be given daily for about 5 days either as an i.v., bolus each day for about 5 days, or as a continuous infusion for about 5 days.

Alternatively, the conjugates can be administered once a week for six weeks or longer. As another alternative, the conjugates can be administered once every two or three weeks. Bolus doses are given in about 50 to about 400 ml of normal saline to which about 5 to about 10 ml of human serum albumin can be added. Continuous infusions are given in about 250 to about 500 ml of normal saline, to which about 25 to about 50 ml of human serum albumin can be added, per 24 hour period. Dosages will be about 10 pg to about 1000 mg/kg per person, i.v. (range of about 100 ng to about 100 mg/kg).

About one to about four weeks after treatment, the patient can receive a second course of treatment. Specific clinical protocols with regard to route of administration, excipients, diluents, dosages, and times can be determined by the skilled artisan as the clinical situation warrants.

Kits

The present invention also provides pharmaceutical kits comprising one or more containers filled with one or more of the ingredients of the pharmaceutical compounds and/or compositions of the present invention, including, one or more targeting ligands and one or more chemotherapeutic agents. Such kits can also include, for example, other compounds and/or compositions, a device(s) for administering the compounds and/or compositions, and written instructions in a form prescribed by a governmental agency regulating the manufacture, use or sale of pharmaceuticals or biological products.

The compounds and conjugates could also be used for the manufacture of a medicament useful for treating or lessening the severity of disorders, such as, characterized by abnormal growth of cells (e.g., cancer).

Cancer therapies and their dosages, routes of administration and recommended usage are known in the art and have been described in such literature as the Physician's Desk Reference (PDR). The PDR discloses dosages of the agents that have been used in treatment of various cancers. The dosing regimen and dosages of these aforementioned chemotherapeutic agents and conjugates that are therapeutically effective will depend on the particular cancer being treated, the extent of the disease and other factors familiar to the physician of skill in the art and can be determined by the physician. For example, the 2006 edition of the Physician's Desk Reference discloses that Taxotere (see p. 2947) is an inhibitor of tubulin depolymerization; Doxorubicin (see p 786), Doxil (see p 3302) and oxaliplatin (see p 2908) are DNA interacting agents, Irinotecal (see p. 2602) is a Topoisomerase I inhibitor, Erbitux (see p 937) and Tarceva (see p 2470) interact with the epidermal growth factor receptor. The contents of the PDR are expressly incorporated herein in their entirety by reference. One of skill in the art can review the PDR, using one or more of the following parameters, to determine dosing regimens and dosages of the chemotherapeutic agents and conjugates, which can be used in accordance with the teachings of this invention.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention.

EXAMPLES

While various embodiments of the present invention have been described above, it should be understood that they have been presented by way of example only, and not limitation. The following non-limiting examples are illustrative of the invention.

Example 1: Novel Enediyne Compounds

Genome Survey of the *Actinomycetale* Collection to Identify Novel Enediyne Producers.

Applying the novel strain prioritization for natural product discovery by a high throughput real-time PCR method, a genome survey of 3,500 strains in the *Actinomycetale* collection was conducted 94 novel enediyne producers were identified (FIGS. 1A-1D). Two sets of PCR primers, specifically targeting E5/E or E/E10, respectively, were designed (FIG. 1A). Genomic DNAs were first prepared for each of the strains in the inventor's collection, normalized their concentrations, and arrayed the DNAs into a 384-well plate format. Real-time PCR was then used, in a 384-well plate format, where specific PCR products were rapidly identified by melting curve analysis (FIG. 1B). The putative hits were confirmed by gel electrophoresis (FIG. 1C), and the identity of hits as the targeted enediyne polyketide (PKS) gene cassettes was finally established by DNA sequencing.

Figures 3A, 3B:
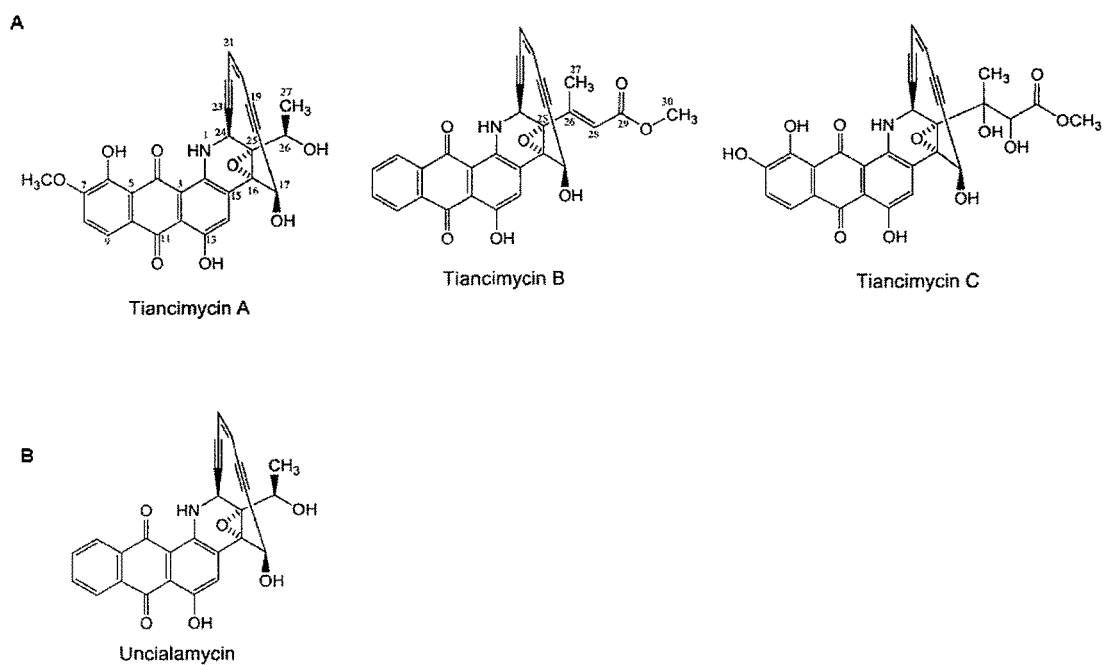
FIGS. 3A-3D show the structural determination of tiancimycin A and B from the S. sp. CB03234 wild-type strain and tiancimycin C from the S. sp. CB03234 ΔtnmH mutant strain and their comparison to the known enediyne natural product uncialamycin.

The two sets of PCR primers, specifically targeting E5/E or E/E10, (FIG. 1A), were complementary. Hits identified by both sets of the primers featured the enediyne PKS gene cassettes with E5/E/E10 clustered together, while hits identified only by one of the two sets of primers featured enediyne PKS gene cassette with either E5 or E10 separated from the E gene. The identity of the enediyne PKS gene cassettes from the 94 new enediyne producers was confirmed by DNA sequencing of E5, E10, and a 1-kb internal fragment of E (FIG. 1A). Phylogenetic analysis of the 94 new enediyne PKS cassettes was conducted, with the 11 known enediyne PKS cassettes as controls, using E5, E10, the 1-kb internal fragment of E, or a combination of thereof, yielding essentially the same outputs. While each of the enediyne PKS cassettes is unique, the phylogenetic tree of the 94 new enediyne PKS cassettes collapsed into 31 distinct clades when subjected to 95% amino acid identity cutoff, yet pairwise comparison of the neighboring clades revealed amino acid sequence identities ranging from 33% to 85% (the pairwise comparison of the 11 known enediyne PKS cassettes revealed amino acid sequence identities ranging from 33% to 69%). It is therefore very significant that 30 of the 31 clades are distinct from the 11 known enediyne PKS cassettes, indicative of novel enediynes. The tiancimycins, a new family of enediyne natural products (FIG. 3A) were produced and isolated from the Streptomyces sp. CB03234 wild-type and ΔtnmH recombinant strains, and characterized.

Genome Sequencing of S. Sp. CB03234 Confirming a Distinct Enediyne Biosynthetic Gene Cluster.

Figure 2:
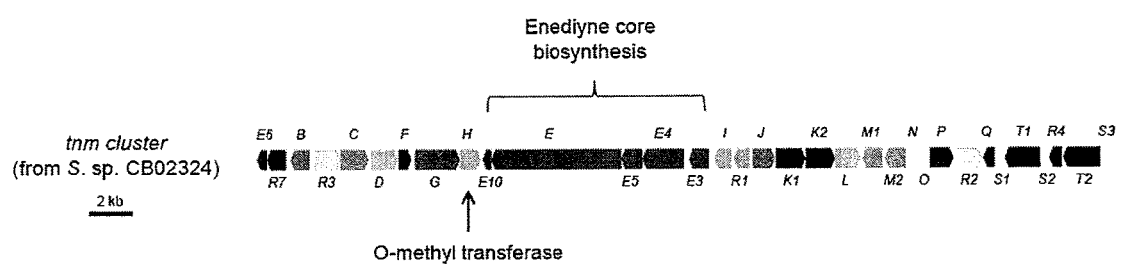
FIG. 2 is a schematic representation showing the genetic organization of the tiancimycin (TNM) biosynthetic gene cluster from S. sp. CB03234. The identity of the TNM gene cluster encoding TNM biosynthesis has been confirmed by (i) inactivation of selected genes encoding the enediyne core biosynthesis abolishing tiancimycin A and B production and (ii) generation of the S. sp. CB03234 ΔtnmH mutant strain that accumulated TNM C.

Genome sequencing of representative hits from the 31 clades were completed, confirming that they each contain an enediyne biosynthetic gene cluster and therefore are true enediyne producers. While these new enediyne gene clusters all feature the characteristic enediyne PKS cassettes, they are rich in open reading frames that are unprecedented in gene clusters that encode production of the known enediynes, promising structural and functional novelty of the encoded new enediyne natural products. These new enediyne gene clusters are distinct to all enediyne biosynthetic gene clusters known to date (FIG. 1D), indicative of novel enediyne natural products as exemplified by the tiancimycin gene cluster from S. sp. CB03234 (FIG. 2).

Fermentation Optimization, Isolation, and Structural Elucidation of Tiancimycins A and B from S. Sp. CB03234 Wild-Type Strain and Tiancimycin C from the ztnmH Mutant Strain:

For tiancimycin production, the S. sp. CB03234 wild-type and ΔtnmH mutant strains were firstly grown on ISP-4 agar medium at 28° C. for 10 days, to obtain fresh spores. For liquid culture, the seed inoculum was prepared by inoculating 50 mL of TSB medium with 1×1 cm block of ISP-4 agar containing the S. sp. CB03234 wild-type or ΔtnmH mutant strain spores and cultured individually by incubating at 28° C. and 250 rpm for 2 days. Then the seed culture (5%) was added to 250 mL baffled Erlenmeyer flasks containing 50 mL of (i) M1 medium [consisting of 1% soluble starch, 0.5% pharmamedia, 0.2% $CaCO_3$, 0.005% $CuSO_4.5H_2O$ and 0.0005% NaI (pH7.0)], (ii) M2 medium [consisting of 6% cane molasses, 2% soluble starch, 2% fish meal, 0.2% $CaCO_3$, 0.01% $CuSO_4.5H_2O$ and 0.0005% NaI (pH7.0)], or (iii) M3 medium [consisting of 2% sucrose, 0.2% bactopeptone, 0.5% cane molasses, 0.5% $CaCO_3$, 0.01% $FeSO_4.7H_2O$, 0.02% $MgSO_4.7H_2O$ and 0.05% KI (pH7.0)] and cultivated at 28° C. and 250 rpm for 6 days. In order to follow the tiancimycin production, 10 µL of the fermentation broth was taken during the fermentation and monitored by the paper-disc agar diffusion bioassay method using Micrococcus luteus ATCC9431 as the indicator organism. Based on the size of the inhibition zone, M1 medium was found to produce the highest amount of tiancimycins and was then used for large scale fermentation. For large scale fermentation, one hundred 2-L baffled Erlenmeyer flasks, each containing 500 mL of M1 medium, were inoculated with 40 mL of the seed culture each and grown at 28° C. and 250 rpm for 6 days.

After the fermentation, the broth was centrifuged at 5000 rpm and 4° C. for 30 min. The supernatant was extracted twice with equal volume of ethyl acetate. The mycelia were treated with ⅒ volume of acetone, after filtration the filtrate was concentrated to dryness in vacuo and then extracted three times with ⅒ volume of water/acetyl acetate (1:1). After separation, the organic phase was combined with the ethyl acetate from the supernatant and concentrated to dryness in vacuo. The oily dark brown residue was dissolved in methanol and subsequently fractionated by MPLC eluted with methanol-$H_2O$ system from 10%-100% using a C18 column. Each fraction was assayed for the activity against M. luteus, and the biologically active fractions were pooled and concentrated to obtain dry powder, which was further purified by Sephadex LH-20 chromatography using methanol to afford pure tiancimycin A and B from the S. sp. CB03234 wild-type strain and tiancimycin C from the S. sp. CB03234 ΔtnmH mutant strain.

Figure 3C:
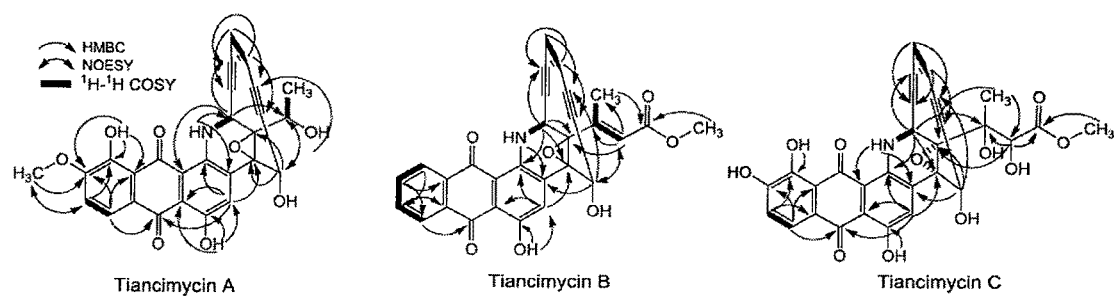
Figure 3D:
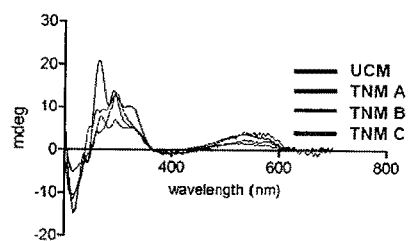

Tiancimycin A was isolated as a purple powder. The molecular formula of tiancimycin A was assigned as $C_{27}H_{19}NO_8$ based on the HRESI mass spectrometric data (m/z 486.1180 [M+H]$^+$, calcd for $C_{27}H_{20}NO_8$, 486.1183 [M+H]$^+$). The $^1$H NMR spectrum of tiancimycin A in DMSO-$d_6$ resembled to that of uncialamycin, suggesting tiancimycin A could be an analogue of uncialamycin. To get the well-resolved NMR signals, 1D and 2D NMR data were thus recorded in acetone-$d_6$ at 700 MHz using a cryoprobe (FIG. 3C, 3D). A pair of mutual coupled olefinic protons at δ 5.96 (H-21) and 6.04 (H-20) with a coupling constant of 10 Hz were assigned to be a cis-disubstituted olefin. The $^3$J HMBC correlations of H-21 with two quaternary carbons at C-23 (δ 98.2) and C-19 (δ 90.2), and H-20 with the other two quaternary carbons C-22 (δ 87.7) and C-18 (δ 99.9) strongly suggested the presence of an enediyne substructure. Further 1D and 2D NMR analysis identified tiancimycin A has the same carbon skeleton as that of uncialamycin (FIG. 3C, 3D). Compared to the molecular formula of uncialamycin ($C_{26}H_{17}NO_6$), tiancimycin A could have one extra hydroxyl group and one extra methoxyl group, which were also revealed by the additional proton signal at 4.01 (3H, s, H-28) and 13.42 (1H, brs, 6-OH) and the absence of two aromatic proton in the $^1$H NMR of tiancimycin A. To assign the location of the methoxyl and hydroxyl groups, the HMBC correlation of OMe/(δ 4.01)/C-7 (δ 154.5); OH (13.42)/C-6 (δ 152.8), C-7 (δ 154.5) and C-5 (δ 116.9), together with a pair of meta-coupled aromatic protons of H-8 (δ 7.41, d, 8.4) and H-9 (δ 7.86, d, 8.4), were observed, indicating the methoxyl and hydroxyl group was substituted at C-7 and C-8, respectively (FIG. 3C, 3D).

Tiancimycin B was isolated as a purple powder with its molecular formular of $C_{29}H_{19}NO_7$ determined by the HRESIMS data (m/z 494.1236 [M+H]$^+$, calcd for $C_{29}H_{20}NO_7$, 494.1235 [M+H]$^+$). A pair of coupled olefinic protons at δ 6.03 (d, J=10.0 Hz, H-21) and 6.14 (d, J=10.0 Hz, H-20), together with the HMBC correlation of H-21 with C-23 (δ 97.8) and C-19 (δ 90.9), and H-20 with the other two quaternary carbons C-22 (δ 89.0) and C-18 (δ 100.1), revealed the presence of an enediyne core substructure similar to that of tiancimycin A. A 1,2-ortho-disubstituted aromatic ring was evidenced by four mutually coupled protons at δ 8.34 (H-6, dd, J=8.3, 2.1 Hz), 7.92 (H-7, t, J=8.3 Hz), 7.94 (H-8, t, J=8.3 Hz), and 8.33 (H-9, dd, J=8.3, 2.1 Hz). The HMBC correlations of H-6/C-4, H-9/C-11, and H-14 (δ 8.64)/C-11 indicated it had the same anthraqunione moiety as that in uncialamycin. A carbonyl ester carbon signal δ 165.8 (C-29) showed the strong HMBC correlation with a singlet δ 3.71 (Me-30), and a weak HMBC correlation with a methyl doublet δ 2.43 (Me-27, J=1.4 Hz), the latter of which was correlated in the COSY spectrum to an olefinic proton at δ 6.54 (H-28, J=1.4), indicating the presence of a methyl but-2-enolate moiety. The further HMBC correlations of Me-27 and H-28 to a quaternary carbon C-25 (δ 75.8), revealing the methyl but-2-enolate moiety is located at C-25 (FIG. 3C, 3D).

The molecular formula of tiancimycin C was determined to be $C_{29}H_{21}NO_{11}$ based on its HRESI MS data (m/z 560.1193 [M+H]$^+$, calcd for $C_{29}H_{22}NO_{11}$ 560.1187 [M+H]$^+$). The enediyne moiety was evidenced by the presence of a pair of cis oriented olefinic protons at δ 6.06 (H-20, J=10.0 Hz) and 5.94 (H-21, J=10.0 Hz), which are correlated with δ 102.3 (C-18), 89.3 (C-22); and 91.3 (C-19) and 97.6 (C-23) in HMBC spectrum, respectively. Three aromatic protons at δ 7.27 (H-8, d, J=8.2 Hz), 7.81 (H-9, d, J=8.2 Hz), and 8.70 (H-14, s) were present in its $^1$H NMR, similar to those in tiancimycin A, evidencing that tiancimycin C has the same substituted pattern in its anthraquinone moiety to that of tiancimycin A. The HMBC correlations of H-8/C-6 (δ 150.9), and H-9/C-7 (δ 152.8) indicated two hydroxyl groups were substituted at C-6 and C-7. The finding of the hydroxyl group at C-7 instead of methoxyl group is consistent with the predicted function of methyltransferase encoded by tnmH. The NH resonance at δ 9.90 showed correlations to C-3 (δ 110.8) and C-15 (δ 135.8); a methine proton at δ 5.19 (H-24) correlated with C-2 (δ 145.0), C-16 (δ 67.8), and C-22 (δ 87.7); and an hydroxylated methine proton at δ 6.27 correlated with C-15 (δ 135.8) and C-19 (δ 91.7) in HMBC spectrum led to the fusion of anthraquinone and enediyne core moieties. The remaining unassigned $C_5H_9O_4$ includes a methyl ($δ_{H-27}$ 1.66, $δ_{C-27}$ 24.9), a methoxyl ($δ_{H-30}$ 3.76, $δ_{C-30}$ 51.7), a methine ($δ_H$ 4.42, $δ_C$ 75.1), a carbonyl carbon ($δ_C$ 172.8), and a hydroxylated quaternary carbon ($δ_C$ 76.9) group. The HMBC correlations observed between H-30 and C-29, and H-27 and C-28 suggested the presence of a methyl 2,3-dihydroxybutanoate side chain. Finally, the side chain was attached to C-25 through C-25-C-26 linkage based on the HMBC correlations of H-24 (δ 5.41) with C-26 (76.5), H-28 (δ 4.42) with C-25 (δ 79.1), and Me-27 (δ 1.66) with C-25 (δ 79.1) (FIG. 3C, 3D). The similar CD curve among tiancimycins A-C and same biosynthetic origin suggested all of them possessed same stereochemistry at C-16, C-17, C-24 and C-25 position (FIG. 3C, 3D). The absolute stereochemistry of uncialamycin has been confirmed by total synthesis. The same R-configuration at C-26 in tiancimycins is further supported by the NOE correlation between H-26 and H-17.

Figures 4A, 4B:
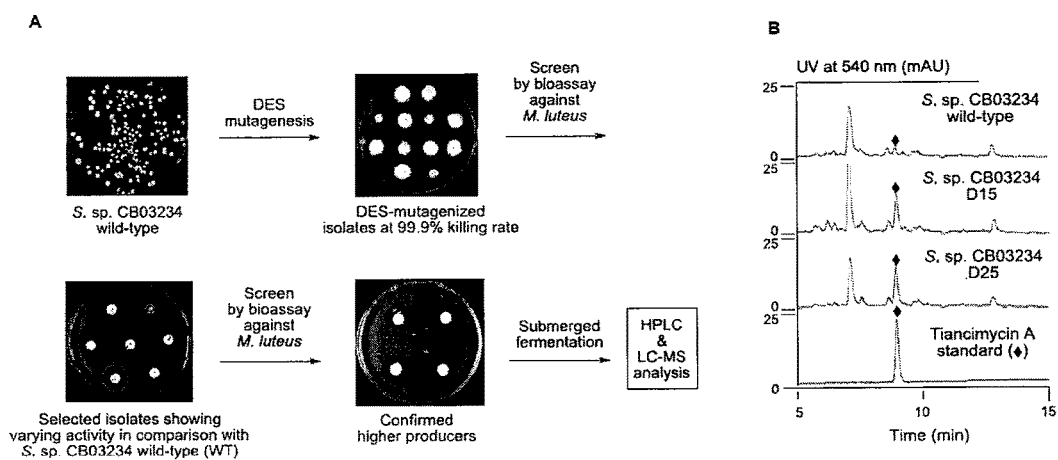
FIGS. 4A-4B show the isolation of tiancimycin-overproducing S. sp. CB03234 strains.

Strain Improvement by Mutagenesis of the S. Sp CB03234 Wild-Type Strain and Isolation of the Tiancimycin High Producers S. Sp CB03234-D15 and CB03234-D25:

The S. sp. CB03234 wild-type strain was originally isolated from an alkaline soil sample from Yuanjiang County, Yunnan Province, China and was subjected to chemical mutagenesis to isolate the tiancimycin higher producers S. sp. CB03234-D15 and CB03234-D25 strains (FIGS. 4A, 4B). Thus, the S. sp. CB03234 wild-type was grown at 28° C. for 10 days on ISP-4 solid medium for sporulation. The spores harvested were suspended in 20% glycerol containing 0.1% Tween 80, and 2 mL of this suspension was mixed with 0.1 mL of diethyl sulfate (DES, alkylating agent); a killing ratio of 99.9% was obtained by shaking the mixture for 1 h at 250 rpm. For each Petri dish, 0.2 mL of the DES-treated spore suspension was spread onto the surface of ISP-4 solid medium. After cultivation for 7-10 days at 28° C., separate colonies appeared. The spores from each of the colonies in the Petri dish were transferred into one corresponding position of the duplicate plates (A and B). The resultant plates were incubated at 28° C. for 10 days.

To screen for the higher producer, each colony in plate (A) was plugged out for bioassay for tiancimycin production, and *M. luteus* ATCC 9431 was used in the bioassay as the test organism. Thus each of the agar plugs were placed onto the bioassay plates seeded with *M. luteus*. The plates were first kept at 4° C. for 2 h to ensure tiancimycin in the agar plug diffusing into the medium of bioassay plates, and the resultant plates were then incubated at 37° C. for 1 day. Control plugs were also prepared with S. sp. CB03234 wild-type using the same procedure. If the strain in one plate (A) showed high tiancimycin productivity by bioassay (i.e., bigger inhibition zone than that from S. sp. CB03234 wild-type) (FIG. 4A), the strain in the corresponding plate (B) will be further validated by submerged fermentation (FIG. 4B).

Positive mutants identified according to bioassay described above were inoculated into a 250 ml Erlenmeyer flask containing 50 mL TSB seed medium, and the flasks were incubated on a rotary shaker at 250 rpm and 28° C. for 2 days. The seed culture (5 mL) was used to inoculate 50 mL production medium in 250 mL baffled flasks and incubated on a rotary shaker at 28° C. and 250 rpm for 7 days. Production medium consist of soluble starch 10 g/L, pharmmedia 5 g/L, $CuSO_4 \cdot 5H_2O$ 0.05 g/L, KI 0.005 g/L, $CaCO_3$ 2 g/L, pH 7.

Following fermentation, the broth (50 mL) was centrifuged to obtain the mycelia and supernatant. The supernatant were extracted twice with equal volume of EtOAc. The mycelia were extracted twice with 15 mL of acetone. The combined EtOAc and acetone extracts were concentrated in vacuo to afford an oily residue. The latter was dissolved in 1 mL MeOH and analyzed by HPLC and LC-MS. The peak area at UV-Vis absorption at 540 nm was used to quantify tiancimycin production on the basis of calibration curves generated with authentic tiancimycin standards.

Of all the colonies screened, two isolates, D15 and D25, afforded reproducible higher tiancimycin titers (FIG. 4A).

D15 and D25 were each subjected to submerged fermentation in triplicates, and tiancimycin productivity in each flask was analyzed by HPLC (FIG. 4B). Tiancimycin titers from S. sp. CB03234-D15 and CB03234-D25 strains were estimated to be ~0.5 mg/L, which is minimally five-fold of that produced by the original S. sp. CB03234 wild-type strain. S. sp. CB03234-D15 and CB03234-D25 strains will be used in the next-run of mutation and strain improvement effort to isolate the desirable higher producer for tiancimycin production needed for preclinical and clinic studies as well as eventual commercialization.

Biological Evaluation of the Tiancimycins as Potent Antitumor Drug Leads:

The in vitro cytotoxic activity ($IC_{50}$, half maximal inhibitory concentration) of the tiancimycins was tested against selected human cancer cell lines, such as breast cancer cells MDA-MB-468, melanoma cell M14 and SK-MEL-5, non-small cell lung cancer cell NCI-H226, central nervous system cell lines SF-295 and SF-539, and the known enediyne UCM was used as a comparison. Suspended cultures of cells were diluted to a concentration of $5\times10^4$ cells $mL^{-1}$ in RPMI 1640 medium supplemented with 10% fetal bovine serum, 100 $\mu gmL^{-1}$ streptomycin, and 100 $UmL^{-1}$ penicillin. The suspended cultures were dispensed into 96-well microtiter plates (100 μL per well) and the plates were incubated for 24 hours at 37° C. in an atmosphere of 5% CO2, 95% air, and 100% humidity. After incubation, original medium was removed and 100 μL of fresh medium was added, followed by adding serial dilutions of the tiancimycins (A, B, and C, 1 μl) and UCM (1 μl) in DMSO. The concentration of the tested compounds was ranged from 0 to 100 nM. Plates were incubated under the above conditions for 72 hours. After incubation, 20 μl CELLTITER 96® AQueous One Solution Reagent (Promega Corp, Madison, Wis., USA) was added to the plates and incubated at 37° C. in a humidified, 5% $CO_2$ atmosphere for 30 to 60 min. The absorbance at 490 nm was recorded using an ELISA plate reader. Each point represents the mean±SD of 3 replicates. The $IC_{50}$ was determined by computerized curve fitting. The tiancimycins are more potent than UCM against the five cell lines tested, serving as outstanding candidates for anticancer drug discovery.

Antitumor activities were assessed using CELLTITER 96® Aqueous One Solution Proliferation Assay (MTS) (Promega Corp.). Cells were plated in 96-well plate at 5000 cells/well and allowed to adhere overnight at 37° C. in a humidified atmosphere of 5% $CO_2$. Medium was then removed and replaced by fresh culture medium containing different concentrations of different drugs. The cells were treated for 72 h before the assay was developed. All assay values were measured in triplicate.

Engineering Tiancimycin Biosynthetic Machinery for the Production of Novel Analogues:

Manipulations of gene encoding natural product biosynthesis for natural product structural diversity have now been well demonstrated. Successful practice for a given natural product requires minimally: (i) availability of the gene cluster encoding the production of the natural product or the family of natural products, (ii) genetic and biochemical characterizations of the biosynthetic machinery for the targeted natural products to a degree that the combinatorial biosynthesis principles can be rationally applied to engineer the novel analogues, (iii) expedient genetic systems for in vivo manipulation of genes governing the production of the target molecules in their native producers or heterologous hosts, and (iv) production of the natural products or their engineered analogues to levels that are appropriate for detection, isolation, and structural and biological characterization. The cloned tiancimycin biosynthetic gene cluster from S. sp. CB03234 sets the stage to engineer the tiancimycin biosynthetic machinery for the production of novel analogues. A general paradigm for enediyne biosynthesis, featuring a convergent biosynthetic strategy, has been well established. An expedient genetic system has been developed for S. sp. CB03234. Tiancimycin titer has been significantly improved and could be improved further by additional rounds of strain improvement experiments. Comparison and contrasting the genes encoding the enediyne core biosynthesis between tiancimycin and other enediyne biosynthetic pathways provide outstanding opportunities to produce tiancimycin analogues with altered enediyne core structures. Engineering the genes encoding the tailoring steps of tiancimycin biosynthesis, such as the O-methyltransferase (TnmH) and cytochrome $P_{450}$ monooxygenase for the anthraquinone moiety, promises to produce novel tiancimycin analogues with altered functional groups, thereby modulating their biological activities or providing reactive chemical handles for further modification by medicinal chemistry, as exemplified by the production of tiancimycin C from then engineered S. sp. CB03234 ΔtnmH recombinant strain (FIG. 3A-3D). The HO— group at C-7 in tiancimycin C should greatly facilitate the conjugation of the tiancimycins to various antibodies of choice to make designer tiancimycin-ADCs.

Analogues that can be accessed by bioengineering, medicinal chemistry, or the combination of both:

TABLE 1

Cytotoxicity of tiancimycin (TNM) A, B, C against selected cancer cell lines in comparison with the known enediyne uncialamycin (UCM).

| Cell lines | Cancer type | TNM A ($IC_{50}$ [nM]) | TNM B ($IC_{50}$ [nM]) | TNM C ($IC_{50}$ [nM]) | UCM ($IC_{50}$ [nM]) |
|---|---|---|---|---|---|
| MDA-MB-468 | Breast | 0.10 ± 0.01 | 0.10 ± 0.01 | 0.07 ± 0.01 | 0.22 ± 0.03 |
| M14 | melanoma | 0.14 ± 0.01 | 0.24 ± 0.01 | 0.25 ± 0.01 | 0.47 ± 0.07 |
| SK-MEL-5 | Melanoma | 0.19 ± 0.01 | 0.19 ± 0.04 | 0.14 ± 0.02 | 1.7 ± 0.1 |
| NCI-H226 | Non-small cell lung | 2.3 ± 0.1 | 2.8 ± 0.1 | 3.3 ± 0.3 | 4.1 ± 0.2 |
| SF-295 | Central nervous system | 0.14 ± 0.01 | 0.26 ± 0.02 | 0.28 ± 0.02 | 0.51 ± 0.05 |
| SF-539 | Central nervous system | 0.30 ± 0.08 | 0.23 ± 0.05 | 0.30 ± 0.05 | 0.67 ± 0.03 |

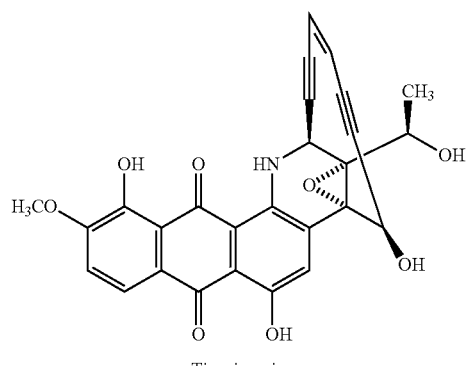

Tiancimycin

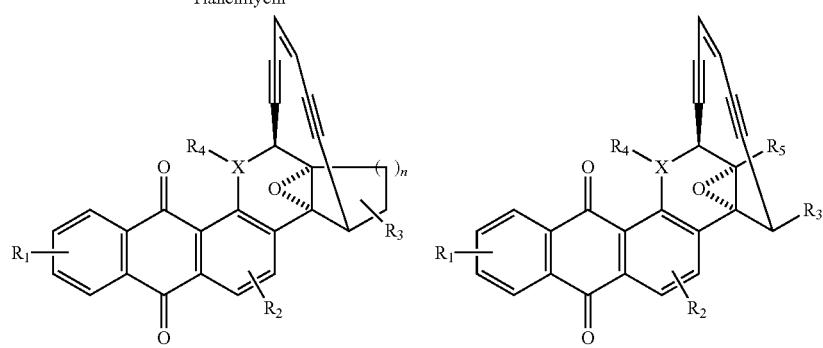

Tiancimycin analogues

X = C, N, S, O

R₁ =
R₂ =
R₃ =     All kinds of C
R₄ =        or
R₅ =     heteroatom
         substitutions Genetic Manipulation of Actinomycetales to Activate Enediyne Biosynthesis and Production.

There are minimally four requirements for implementing metabolic pathway engineering strategies to natural product discovery and structural diversity. These are: (i) the gene clusters encoding the production of a particular natural product or family of natural products, (ii) genetic and biochemical characterizations of the biosynthetic machinery for the targeted natural products to a degree that combinatorial biosynthesis principles can be rationally applied to engineer the novel analogues, (iii) expedient genetic systems for in vivo manipulation of genes governing the production of the target molecules in either native producers or heterologous hosts, and (iv) production of the natural products or engineered analogues to levels that are sufficient for isolation and structural and biological characterization. Although each of these requirements is essential, establishing an expedient genetic system for in vivo manipulation of the biosynthetic machinery of the targeted metabolites is important (Galm U., Shen, B. *Exp. Opinion Drug Dis.* 2006, 1, 409-437; Van Lanen S. G., Shen, B. *Drug Disc. Today: Technologies* 2006, 3, 285-292; Van Lanen, S. G.; Shen, B. *Curr. Opinion Drug Discov. Develop.* 2008, 11, 186-195). Thus, a decision and opportunity for innovation in manipulating enediyne biosynthesis is the selection of the producers that are compatible with the expedient technologies and tools of recombinant DNA work in *Streptomyces* species and related organisms that have been developed in the past two decades. The CAL, DYN, and ESP (partial) clusters were cloned from *M. echinospora, M. chersina,* and *A. verrucosospora*, respectively, and genetic manipulations in *Micromonospora* and *Actinomadura* are known to be notoriously difficult. As a result, the ESP cluster is incomplete, and the boundaries of both the CAL and DYN clusters have yet to be determined experimentally. In contrast, biosynthesis and engineering of C-1027, NCS, and UCM have been greatly facilitated by the expedient genetic systems in *S. globisporus, S. carzinostaticus,* and *S.* sp., respectively. Accordingly, *Streptomyces* in the *Actinomycetale* strain collection was selected, and this selection is vital to overcoming the current challenges of, and meeting future objectives for, enediyne discovery, biosynthesis, and engineering in their native producers.

Development of the Probes to Survey Bacterial Genomes for Enediyne PKS Gene Cassettes.

Comparative bioinformatics analyses of the four 9- (NCS, C-1027, MDP, KED) and four 10-membered (CAL, DYN, UCM, ESP) enediyne PKS loci, as well as the three loci encoding the biosynthesis of sporolides (SPO) and cyanosporasides (CYA, CYN), revealed a set of five genes common to all enediynes (i.e., the enediyne PKS gene cassette consisting of E3/E4/E5/E/E10); no apparent conservation was observed beyond the enediyne PKS gene cassettes, accounting for the structural diversity characteristic for the periphery moieties of the enediynes. This remarkable sequence homology and organizational conservation prompted the selection of genes within the enediyne PKS cassettes as probes to survey genomes for the presence of enediyne biosynthetic machinery.

Actinomycetales as the Most Prolific Enediyne Producers.

To validate the utility of the selected genes within the enediyne PKS cassette as probes, a virtual survey of the entire GenBank was carried out, using each of the five genes within the enediyne cassette, alone or in combination, as queries, for genes encoding enediyne biosynthetic machineries. Several important lessons were learned from these surveys. (i) All 11 confirmed enediyne biosynthetic machineries were identified, validating the utility and specificity of the genes with the enediyne PKS cassette as probes. (ii) While each of the five genes alone yields essentially the same outputs, E5, E, or E10 were preferred, and the combination of E5/E or E/E10 afforded the best results. (iii) Together with the 11 known enediyne biosynthetic machineries, 55 additional enediyne PKS cassettes were also identified from organisms not known as enediyne producers, consistent with the early findings that the biosynthetic potential of enediynes is significantly underappreciated (i.e., a total of 66 enediyne biosynthetic loci from the publicly accessible GenBank database as of Feb. 24, 2014). (iv) All of the 66 loci are of bacterial origin, and most remarkably, 55 of the 66 loci are in the order of Actinomycetales, revealing the Actinomycetales as the most prolific enediyne producers.

A High-Throughput Method to Survey *Actinomycetale* Genomes for Novel Enediyne Producers.

Inspired by the accuracy and specificity observed in the virtual screening, a high-throughput method was developed to survey the genes encoding the enediyne PKS cassettes and applied it to the *Actinomycetale* collection to identify potential new enediyne producers. (i) Close examination of the enediyne PKS gene cassettes showed that, while the five genes are absolutely conserved among 10 of the 11 known enediynes (the ESP cluster is incomplete hence cannot be included for comparison), there are subtle variations in their relative organization—(a) E5/E/E10 all clustered (as in NCS, MDP, SPO, CYA, CAL, DYN, UCM, ESP), (b) E5/E clustered but E10 separated (as in C-1027), or (c) E/E10 clustered but E5 separated (as in KED, CYN). Two sets of PCR primers were designed, specifically targeting E5/E or E/E10, respectively. (ii) The feasibility to amplify the enediyne PKS gene cassettes by PCR was shown but these early experiments were low throughput, requiring analysis of each of the PCR products by gel electrophoresis. To develop a high-throughput method, genomic DNAs were prepared for each of the strains in the collection, normalized their concentrations, and arrayed the DNAs into a 384-well plate format. Real-time PCR was chosen, in a 384-well plate format, where specific PCR products were rapidly identified by melting curve analysis. The putative hits were then confirmed by gel electrophoresis, and the identity of hits as the targeted enediyne PKS gene cassettes was finally established by DNA sequencing.

What is claimed:

1. An enediyne compound comprising a structure represented by formula (I):

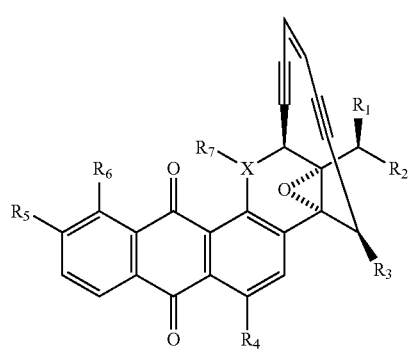

(I)

or a pharmaceutically acceptable salt thereof, wherein:

$R_1$, $R_2$, $R_3$, $R_4$, are each independently: H, OH, F, Cl, Br, R', OR', $CH_3$, $NH_2$, NHR', $NR'_2$, SH, SR', C(O)R, $RCO_2R'$, halogen, or alkyl;

$R_5$ and $R_6$ are each independently OH, F, Cl, Br, OR', $NH_2$, NHR', $NR'_2$, SH, SR', C(O)R, $RCO_2R'$;

$R_7$ is H or alkyl;

R' and R are independently: H, $C_1$-$C_{10}$ alkyl, or aryl;

X is N.

2. The enediyne compound of claim 1, wherein the enediyne compound is

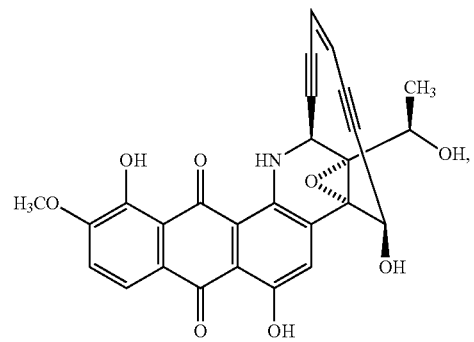

or pharmaceutically acceptable salts thereof.

3. The enediyne compound of claim 1, wherein the enediyne compound is:

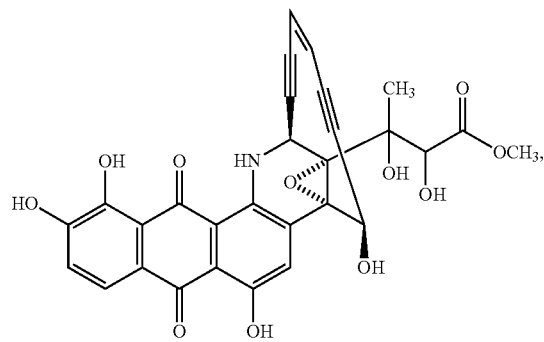

or pharmaceutically acceptable salts thereof.

4. The enediyne compound of claim 1, wherein the compound is associated with a ligand, the ligand comprising: antibodies, antibody fragments, aptamers, peptides, polypeptides, carbohydrates, oligonucleotides or small molecular weight (MW) compounds.

5. The enediyne compound of claim 1, wherein the ligand specifically binds a tumor antigen or a target molecule or cell associated with a disease.

* * * * *

UNITED STATES PATENT AND TRADEMARK OFFICE
CERTIFICATE OF CORRECTION

PATENT NO. : 10,336,766 B2
APPLICATION NO. : 15/541904
DATED : July 2, 2019
INVENTOR(S) : Ben Shen Page 1 of 1

It is certified that error appears in the above-identified patent and that said Letters Patent is hereby corrected as shown below:

In the Specification

Column 1, Line 9, insert the following paragraph:
-- STATEMENT OF GOVERNMENT LICENSE RIGHTS
This invention was made with government support under grant numbers CA078747, GM086184, and AI079070 awarded by the National Institutes of Health. The government has certain rights in the invention. --

Signed and Sealed this
Seventh Day of April, 2020

Andrei Iancu
*Director of the United States Patent and Trademark Office*